US012674213B2

(12) United States Patent　　　　(10) Patent No.:　US 12,674,213 B2

Doddareddy et al.　　　　　　　　　(45) Date of Patent:　Jul. 7, 2026

---

(54) COMPOSITIONS AND METHODS FOR QUANTIFYING INTEGRATION OF RECOMBINANT VECTOR NUCLEIC ACID

(71) Applicant: Janssen Biotech, Inc., Horsham, PA (US)

(72) Inventors: Rajitha Doddareddy, Fort Washington, PA (US); Hsing-Yin Liu, Voorhees, NJ (US); Levi Gray-Rupp, Philadelphia, PA (US); Tong-Yuan Yang, Chadds Ford, PA (US)

(73) Assignee: Janssen Biotech, Inc., Horsham, PA (US)

( * ) Notice: Subject to any disclaimer, the term of this patent is extended or adjusted under 35 U.S.C. 154(b) by 797 days.

(21) Appl. No.: 17/194,699

(22) Filed: Mar. 8, 2021

(65) Prior Publication Data

US 2021/0332448 A1　　Oct. 28, 2021

Related U.S. Application Data

(60) Provisional application No. 63/148,300, filed on Feb. 11, 2021, provisional application No. 62/987,019, filed on Mar. 9, 2020.

(51) Int. Cl.
　　*C12Q 1/70*　　　　(2006.01)
(52) U.S. Cl.
　　CPC ............. *C12Q 1/703* (2013.01); *C12Q 1/701* (2013.01); *C12Q 2600/156* (2013.01)
(58) Field of Classification Search
　　None
　　See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis | |
| 4,965,188 A | 10/1990 | Mullis et al. | |
| 5,210,015 A | 5/1993 | Gelfand et al. | |
| 5,399,491 A | 3/1995 | Kacian et al. | |
| 5,854,033 A | 12/1998 | Lizardi | |
| 5,994,136 A | 11/1999 | Naldini et al. | |
| 6,013,516 A | 1/2000 | Verma et al. | |
| 6,174,670 C1 | 1/2001 | Wittwer et al. | |
| 2019/0100812 A1 * | 4/2019 | Wuitschick ............. | C12Q 1/703 |
| 2019/0284610 A1 | 9/2019 | Hefner et al. | |

FOREIGN PATENT DOCUMENTS

| | | | | | |
|---|---|---|---|---|---|
| CN | 113185616 | * | 8/2017 | | |
| JP | 4262799 B2 | | 5/2009 | | |
| WO | WO-9416060 A1 * | | 7/1994 | ............. | A61K 35/14 |
| WO | WO 2009/019612 A2 | | 2/2009 | | |
| WO | WO 2016/187151 A1 | | 11/2016 | | |
| WO | 2017025038 A1 | | 2/2017 | | |
| WO | 2018028647 A1 | | 2/2018 | | |
| WO | WO 2019/183025 A1 | | 9/2019 | | |
| WO | WO-2020020359 A1 * | | 1/2020 | ............. | A61K 35/17 |
| WO | 2020033916 A1 | | 2/2020 | | |
| WO | WO 2021/038524 A1 | | 3/2021 | | |

OTHER PUBLICATIONS

Sherman et al., Molecular Therapy: Methods & Clinical Development, Mar. 2017, 4:39-49. (Year: 2017).*

Scholler et al., Sci Transl Med, May 2, 2012, 4(132):132ra53. (Year: 2012).*

Barczak et al., Mol Biotechnol, 2015, 57:195-200. (Year: 2015).*

Moens et al., J Clin Microbiol., Nov. 2009, 47(11):3682-3691. (Year: 2009).*

Yu et al., Virology, 2008, 379(1):78-86. (Year: 2008).*

Avettand-Fènoël, et al., "LTR Real-Time PCR for HIV-1 DNA Quantitation in Blood Cells for Early Diagnosis in Infants Born to Seropositive Mothers Treated in HAART Area (ANRS CO 01)", (2009), Journal of Medical Virology, vol. 81, pp. 217-223.

Charrier, S., et al., "Quantification of lentiviral vector copy numbers in individual hematopoietic colony-forming cells shows vector dose-dependent effects on the frequency and level of transduction", (2011), Gene Therapy, vol. 18, pp. 479-487.

Day, E., et al., "Digital PCR strategies in the development and analysis of molecular biomarkers for personalized medicine", (2013), Methods, vol. 59, pp. 101-107.

Dull, T., et al., "A Third-Generation Lentivirus Vector with a Conditional Packaging System", (1998), Journal of Virology, vol. 72, No. 1, pp. 8463-8471.

Ertl, R., et al., "Viral transcriptome analysis of feline immunodeficiency virus infected cells using second generation sequencing technology", (2011), Veterinary Immunology and Immunopathology, vol. 143, pp. 314-324.

Hindson, B.J., et al., "High-Throughput Droplet Digital PCR System for Absolute Quantitation of DNA Copy Number", (2011), Anal. Chem., vol. 83, pp. 8604-8610.

Jena, B., et al., "Redirecting T-cell specificity by introducing a tumor-specific chimeric antigen receptor", (2010), Blood, vol. 116, No. 7, pp. 1035-1044.

Kohn, D.B., et al., "CARs on Track in the Clinic", (2011), Molecular Therapy, vol. 19, No. 3, pp. 432-438.

Kutner, R.H., et al., "Simplified production and concentration of HIV-1-based lentiviral vectors using HYPERFlask vessels and anion exchange membrane chromatograph", (2009), BMC Biotechnology, vol. 9, No. 10, pp. 1-7.

Kutner, R.H., et al., "Production, concentration and titration of pseudotyped HIV-1-based lentiviral vectors", (2009), Nature Protocols, vol. 4, No. 4, pp. 495-505.

(Continued)

*Primary Examiner* — Nicole Kinsey White

(74) *Attorney, Agent, or Firm* — TROUTMAN PEPPER LOCKE LLP

(57) ABSTRACT

In certain aspects, the disclosure relates to methods of quantifying integration of a recombinant vector nucleic acid into a target cell's genome. The present disclosure also provides compositions and kits, including particular primers and probes, for performing the quantitation.

46 Claims, 4 Drawing Sheets

Specification includes a Sequence Listing.

(56) References Cited

OTHER PUBLICATIONS

Lee, L.G., et al., "New energy transfer dyes for DNA sequencing", (1997), Nucleic Acids Research, vol. 25, No. 14, pp. 2816-2822.

Lizée, G., et al., "Real-Time Quantitative Reverse Transcriptase-Polymerase Chain Reaction as a Method for Determining Lentiviral Vector Titers and Measuring Transgene Expression", (2003), Human Gene Therapy, vol. 14, pp. 497-507.

Logan, A.C., et al., "Integrated Self-Inactivating Lentiviral Vectors Produce Full-Length Genomic Transcripts Competent for Encapsidation and Integration", (2004), Journal of Virology, vol. 78, No. 16, pp. 8421-8436.

Naldini, L., et al., "In Vivo Gene Delivery and Stable Transduction of Nondividing Cells by a Lentiviral Vector", (1996), Science, vol. 272, pp. 263-267.

Naldini, L., et al., "Lentiviruses as gene transfer agents for delivery to non-dividing cells", (1998), Current Opinion in Biotechnology, vol. 9, pp. 457-463.

Pekin, D., et al., "Quantitative and sensitive detection of rare mutations using droplet-based microfluidics", (2011), Lab Chip, vol. 11, pp. 2156-2166.

Pinheiro, L.B., et al., "Evaluation of a Droplet Digital Polymerase Chain Reaction Format for DNA Copy Number Quantification", (2012), Anal. Chem., vol. 84, pp. 1003-1011.

Pohl, G., et al., "Principle and applications of digital PCR", (2004), Expert Rev. Mol. Diagn., vol. 4, No. 1, pp. 41-47.

Sadelain, M., et al., "The Basic Principles of Chimeric Antigen Receptor Design", (2013), Cancer Discovery, vol. 3, No. 4, pp. 388-398.

Siegel, R., et al., "Cancer Statistics, 2012", (2012), CA: A Cancer Journal of Clinicians, vol. 62, pp. 10-29.

Titov, A., et al., "Advancing CAR T-Cell Therapy for Solid Tumors: Lessons Learned from Lymphoma Treatment", (2020), Cancers, vol. 12, pp. 1-22.

Zhao, Y., "Development of the First World Health Organization Lentiviral Vector Standard: Toward the Production Control and Standardization of Lentivirus-Based Gene Therapy Product", (2017), Human Gene Therapy Methods, vol. 28, No. 4, pp. 205-214.

Zufferey, R., et al., "Multiply attenuated lentiviral vector achieves efficient gene delivery in vivo", (1997), Nature Biotechnology, vol. 15, pp. 871-874.

International Search Report from PCT/EP2021/055816 mailed Jun. 25, 2021.

Riviere et al., "Analysis of the Viral Elements Required in the Nuclear Import of HIV-1 DNA," Journal of Virology (Jan. 31, 2010) vol. 84, No. 2, pp. 729-739.

* cited by examiner

COMPOSITIONS AND METHODS FOR QUANTIFYING INTEGRATION OF RECOMBINANT VECTOR NUCLEIC ACID

RELATED APPLICATIONS

This application claims the benefit of U.S. Provisional Application No. 62/987,019, filed Mar. 9, 2020, and U.S. Provisional Application No. 63/148,300, filed Feb. 11, 2021, which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 24, 2021, is named PRD4079USNP1_SL.txt and is 21,376 bytes in size.

BACKGROUND

Recent advances in the understanding of the delivery of genomic material and integration into a target cell's genome have great potential to transform the standard-of-care for a variety of diseases. Chimeric antigen receptor ("CAR") T-cell therapy has shown potential to treat B cell malignancies and other cancers, such as lymphoblastic leukemia, B-cell lymphoma, sarcoma, neuroblastoma, and certain solid tumor cancers (see, e.g., Sadelain et al., Cancer Discovery 3:388-398 (2013) and Titov et al., Cancer 12: 125-146 (2020)), and generally involves modification of T-cells in vitro to generate CAR expressing T-cells. Most approaches to genetic manipulation of T cells engineered for human application have used retrovirus, such as lentivirus, for the stable expression of chimeric antigen receptor (CAR) (Jena et al., 2010; Ertl et al., 2011; Kohn et al., 2011). However, one of the challenges of current integration techniques using viral vector delivery is determining whether the vector has not only entered the cells but also whether the transgene successfully incorporated into the host genome (a process called "viral integration") and how many times (or the frequency of viral integration).

Southern blots were initially the preferred technique to measure the integration of retroviral vector sequence copy numbers, but are slow and expensive due to the manual labor required. Recently, researchers have developed quantitative PCR ("qPCR") methods to determine transduction efficiency and copy number. Some methods do not differentiate free, unincorporated vector from integrated, and thus are only an estimation of the copy number. See e.g., Charrier et al. Gene Therapy 18: 479-487 (2011). Some other methods use primers specific to a particular transgene. See *Hum. Gene Ther.* 14: 497-507 (2003). However, these methods either do not generate an exact copy number, or are costly due to the need to design different primers specific for each transgene.

SUMMARY OF THE INVENTION

The disclosure provides methods of quantitating integration of a recombinant vector nucleic acid (typically including a transgene) into a target cell's genome, which methods are not limited by or specific to any particular transgenes. The present disclosure also provides compositions and kits, including particular primers and probes, for performing the quantitation.

In one aspect, the disclosure provides a method of quantifying integration of a recombinant vector nucleic acid into a cellular genome, the method comprising: (a) providing a biological sample comprising a host cellular genome; (b) amplifying genomic DNA of the biological sample with quantitative amplification technique using a primer pair comprising a first oligonucleotide primer and a second oligonucleotide primer, wherein at least one oligonucleotide primer of the primer pair specifically hybridizes to an integrated recombinant vector polynucleotide sequence; and (c) quantifying the genomic nucleic acid that was amplified through step (b).

In some embodiments, quantifying comprises determining the copy number. In some embodiments, the quantitative amplification technique is quantitative PCR. In some embodiments, the quantitative amplification technique is digital PCR. In some embodiments, the quantitative amplification technique is droplet digital PCR. In some embodiments, the quantitative amplification technique is end point PCR.

In certain embodiments, quantifying integration of the recombinant vector nucleic acid in the host cellular genome further comprises comparing the integrated recombinant vector sequence copy numbers of the biological sample to a reference polynucleotide sequence. In some embodiments, the reference polynucleotide sequence encodes a housekeeping protein. In some embodiments, the housekeeping protein is albumin. In some embodiments, the integrated recombinant vector sequence copy number and the reference polynucleotide sequence copy number are measured in multiplex. In some embodiments, the integrated recombinant vector sequence copy number and the reference polynucleotide sequence copy number are measured in singleplex.

In some embodiments, the method further comprises evaluating the validity of an assay for quantifying the integration of a recombinant vector nucleic acid by assessing one or more assay acceptance criteria selected from the group consisting of: (a) the threshold cycle of both the provirus and the reference polynucleotide sequence in all the replicates of a control containing no template DNA is undeterminable; (b) the correlation coefficient for the standard curves of both the provirus and the reference polynucleotide sequence, generated by linear regression using the standard samples, is greater than or equal to 0.97; (c) the estimated copy values for provirus and reference polynucleotide sequence from the slope of said standard curves indicates a PCR efficiency of between 90% and 110%; (d) the threshold cycle of both the provirus and the reference polynucleotide sequence in none of the replicates of any of the standard samples is undeterminable; (e) the mean threshold cycle of both the provirus and the reference polynucleotide sequence in the base standard sample is less than or equal to 22.0; (f) the standard deviation in the threshold cycle of both the provirus and the reference polynucleotide sequence in each standard sample is less than or equal to 0.60; (g) the average measured copies of the reference polynucleotide sequence for the one or more positive control samples is within 30% of the nominal expected value; (h) the measured mean VCN/cell value for the one or more positive control samples is within 30% of the nominal expected VCN/cell value for each control; and (i) the coefficient of variation of the VCN/cell value for the one or more positive control samples is less than or equal to 20%.

In some embodiments, the method further comprises evaluating the validity of the quantification of the integration of a recombinant vector nucleic acid for a sample by assessing one or more sample acceptance criteria selected from the group consisting of: (a) the average copy value of the reference polynucleotide sequence in the sample is within 30% of the expected value of 30,303.030 copies; (b) if the sample has a genomic DNA (gDNA) concentration less than 0.02 µg/µL, the expected copies of the reference polynucleotide sequence for that sample is calculated from the amount of DNA actually loaded into the reactions; (c) the mean target provirus copy value in the sample is between the validated range of the copy value for the assay; (d) the mean target provirus copy value in the sample is between 121, 212.121 and 193.939 copies; (e) the coefficient of variation of the VCN/cell value for the replicates of the target sample is less than or equal to 20%; and (f) the standard deviation in the cycle threshold of both the target provirus and the target reference polynucleotide sequence in the sample is less than or equal to 0.60.

In some embodiments, the recombinant vector contains a transgene. In some embodiments, the recombinant vector is a gene therapy vector. In some embodiments, the recombinant vector is a viral vector. In some embodiments, the recombinant vector is a retroviral vector. In some embodiments, the retroviral vector is a lentiviral vector. In some embodiments, the lentivirus that the lentiviral vector is based on is human immunodeficiency virus 1 (HIV-1), or human immunodeficiency virus 2 (HIV-2).

In some embodiments, the method of quantifying integration of a recombinant vector nucleic acid into a cellular genome further comprises a method for identification of the transgene. In some embodiments, the method for identification of the transgene comprises: (a) providing a biological sample comprising a host cellular genome; (b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to the transgene; and (c) detecting and/or quantifying the genomic nucleic acid that was amplified through step (b). In some embodiments, the transgene is a polypeptide encoded by a nucleic acid sequence comprising the sequence of SEQ ID NO: 19 or 21.

In some embodiments, the oligonucleotide primer that specifically hybridizes to an integrated recombinant vector polynucleotide sequence comprises the nucleic acid sequence of SEQ ID NO:1, SEQ ID NO: 5, or SEQ ID NO: 14. In some embodiments, the second oligonucleotide primer for amplifying the recombinant vector nucleic acid comprises the nucleic acid sequence of SEQ ID NO:2, SEQ ID NO: 6, or SEQ ID NO: 15.

In some embodiments, the oligonucleotide primer that specifically hybridizes to an integrated recombinant vector polynucleotide sequence specifically hybridizes to an LTR sequence of the integrated recombinant vector sequence. In some embodiments, the oligonucleotide primer that specifically hybridizes to an integrated lentiviral vector polynucleotide sequence specifically hybridizes to the U3 region of the 5'LTR of a lentiviral vector nucleic acid sequence. In some embodiments, the oligonucleotide primer that specifically hybridizes to an integrated lentiviral vector polynucleotide sequence specifically hybridizes to the U3 region and R region of the 5'LTR of a lentiviral vector nucleic acid sequence. In some embodiments, the oligonucleotide primer that specifically hybridizes to an integrated lentiviral vector polynucleotide sequence specifically hybridizes to the PBS region of the 5'LTR of a lentiviral vector nucleic acid sequence. In some embodiments, the oligonucleotide primer that specifically hybridizes to an integrated lentiviral vector polynucleotide sequence specifically hybridizes to the psi (Ψ) packaging signal. In certain embodiments, the primer will not specifically hybridize to the naturally occurring retroviral nucleic acid sequence.

In some embodiments, the method utilizes a detectable nucleic acid probe that specifically hybridizes to the amplified recombinant vector nucleic acid. In some embodiments, the probe that specifically hybridizes to the recombinant vector nucleic acid comprises the nucleic acid sequence of SEQ ID NO: 3, SEQ ID NO: 4, SEQ ID NO: 7, or SEQ ID NO: 16. In some embodiments, the probe for the integrated recombinant vector nucleic acid specifically hybridizes to an LTR sequence of the integrated recombinant vector nucleic acid. In some embodiments, the probe for the lentiviral vector nucleic acid used in step (b) specifically hybridizes to the U3 region and R region of the 5'LTR of the lentivirus. In some embodiments, the probe for the lentiviral vector nucleic acid used in step (b) specifically hybridizes to the U5 region and PBS region of the 5'LTR of the lentivirus. In some embodiments, the probe for the lentiviral vector nucleic acid used in step (b) specifically hybridizes to the PBS region of the 5'LTR of the lentivirus. In some embodiments, the probe for the lentiviral vector nucleic acid used in step (b) specifically hybridizes to the R region and U5 region of the 5'LTR of the lentiviral vector nucleic acid sequence. In certain embodiments, step (b) utilizes an intercalating dye. In some embodiments, the intercalating dye is SYBR green.

In some embodiments, the biological sample is a cell sample or a tissue sample. Specifically, in some embodiments, the tissue sample is blood, plasma, serum, saliva or a tissue biopsy. In some embodiments, the sample is from a subject. In some embodiments, the subject is a human. In some embodiments, the recombinant vector nucleic acid sequence comprises a transgene. In some embodiments, the transgene encodes a chimeric antigen receptor. In some embodiments, the chimeric antigen receptor comprises the amino acid sequence of SEQ ID NO: 18, SEQ ID NO: 20, or SEQ ID NO: 22. In some embodiments, the chimeric antigen receptor is a polypeptide encoded by a nucleic acid sequence comprising the sequence of SEQ ID NO: 19 or SEQ ID NO: 21. In some embodiments, the chimeric antigen receptor recognizes BCMA, KLK2 or GPRC5D.

In some embodiments, the method further comprises simultaneously utilizing at least one pair of oligonucleotide primers that specifically amplify a reference polynucleotide sequence.

In still another aspect, the disclosure provides a method for monitoring transduction efficiency of a recombinant vector nucleic acid, comprising, a) providing one or more biological samples containing genomic DNA transduced by a recombinant vector nucleic acid, wherein a portion of the recombinant vector nucleic acid is integrated into the genomic DNA; and b) quantifying the recombinant vector nucleic acid integrated in the host cellular genome according to the methods of the disclosure. In some embodiments, the method further comprises comparing the recombinant vector sequence copy numbers of the biological sample to a reference.

In yet another aspect, the disclosure provides a method of lot release testing for a cell product transduced by a recombinant vector, comprising a) providing one or more biological samples of a cell product containing genomic DNA transduced by a recombinant vector from each lot; b) quantifying the recombinant vector nucleic acid integrated in the host cellular genome in each biological sample according to the methods of the disclosure; c) comparing the integrated recombinant vector sequence copy numbers quantified in step (b) for the biological samples to a reference; and d) releasing lots where the integrated recombinant vector sequence copy numbers pass predetermined criteria.

In another aspect, the disclosure provides a method of quantifying integration of a retroviral vector nucleic acid into a cellular genome, the method comprising: (a) providing a biological sample comprising a host cellular genome; (b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to an integrated retroviral vector polynucleotide sequence; and (c) quantifying the genomic nucleic acid that was amplified through step (b), wherein quantifying integration of the retroviral vector nucleic acid into the host cellular genome comprises comparing the ratio of amplified retroviral vector nucleic acid to a reference, wherein the retroviral vector nucleic acid is a lentiviral vector sequence, and wherein the oligonucleotide primer pair comprise the nucleic acid sequence of SEQ ID NO:1 and the nucleic acid sequence of SEQ ID NO:2, respectively, or the nucleic acid sequence of SEQ ID NO:5 and the nucleic acid sequence of SEQ ID NO:6, respectively, or the nucleic acid sequence of SEQ ID NO:14 and the nucleic acid sequence of SEQ ID NO:15, respectively. In certain embodiments, the quantification uses a detectable probe comprising the nucleic acid sequence of SEQ ID NO: 3, SEQ ID NO: 4, SEQ ID NO: 7, or SEQ ID NO: 16. In another aspect, the disclosure provides an oligonucleotide comprising the nucleic acid sequence of SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 14, SEQ ID NO: 15, or SEQ ID NO: 16.

In another aspect, the disclosure provides a kit for measuring integrated recombinant vector nucleic acid sequence copy number, comprising: a primer of a primer pair that specifically hybridizes to an integrated recombinant vector nucleic acid, wherein the primer pair specifically amplifies a portion of the integrated recombinant vector nucleic acid; and a detectable nucleic acid probe that specifically hybridizes to the amplified recombinant vector nucleic acid.

In another aspect, the disclosure provides a kit for measuring integrated recombinant vector nucleic acid sequence copy number, comprising: a forward primer that specifically hybridizes to an integrated recombinant vector nucleic acid comprising the nucleic acid sequence of SEQ ID NO:1, SEQ ID NO: 5, or SEQ ID NO: 14; a reverse primer that specifically hybridizes to an integrated recombinant vector nucleic acid comprising the nucleic acid sequence of SEQ ID NO: 2, SEQ ID NO: 6, or SEQ ID NO: 15, and a detectable probe comprising the nucleic acid sequence of SEQ ID NO: 3, SEQ ID NO: 4, SEQ ID NO: 7, or SEQ ID NO: 16.

The disclosure contemplates all combinations of any of the foregoing aspects and embodiments, as well as combinations with any of the embodiments set forth in the detailed description and examples.

BRIEF DESCRIPTION OF THE DRAWINGS

For the purpose of illustrating the invention, there are depicted in the drawings certain embodiments of the disclosure. However, the disclosure is not limited to the precise arrangements and instrumentalities of the embodiments depicted in the drawings.

DETAILED DESCRIPTION OF THE INVENTION

Overview

Figures 1A, 1B:
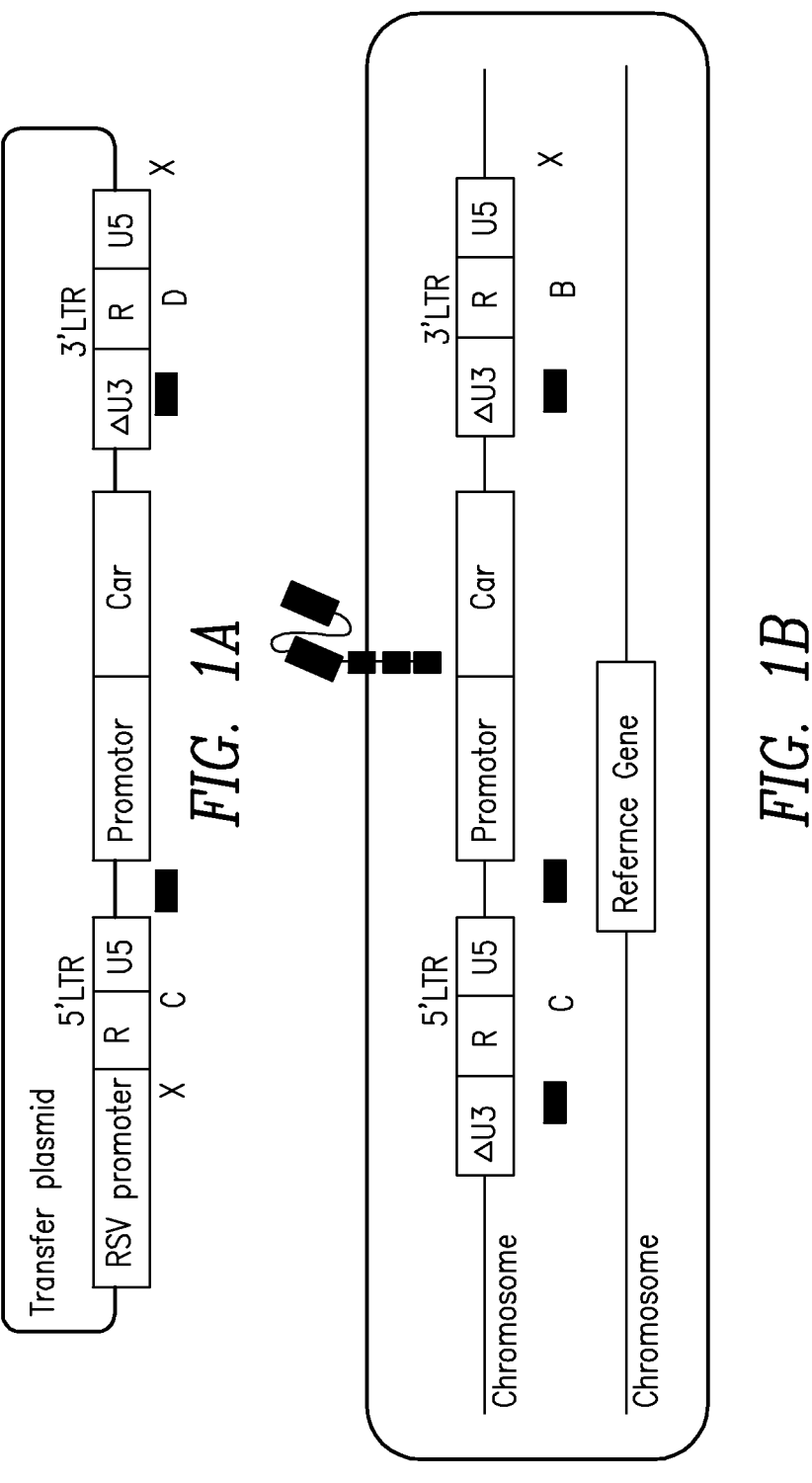
FIG. 1A shows an exemplary lentiviral vector transfer plasmid that includes a transgene encoding a chimeric antigen receptor (CAR).
FIG. 1B depicts a cell following integration of a portion of said vector into a target cell, and expression of the integrated transgene at the cell surface. As depicted in panel 1A, the lentiviral vector transgene encodes a CAR flanked by a 5'-LTR (Site C) and 3'-LTR (Site D). As depicted in panel 1B, when the lentiviral vector is incorporated into the cell's genome, a portion of the 5'-LTR region (Site A) has been replaced with the ΔU3 portion of the 3'-LTR sequence. Rectangle black box indicates exemplary primer and/or probe binding sites and 'X' indicates the lack of primer binding site to make a quantifiable amplicon. The integrated 5'-LTR (Site A) has a ΔU3 site while the transfer plasmid 5'-LTR (Site C) does not.

The invention provides a method for detecting and/or quantifying integration of recombinant vector nucleic acids, and thus, the transgenes delivered into a host cell's genome. There is a need for specific detection and/or quantification of recombinant vector delivered transgene sequences in transduced cells, such as CAR-T cells. To this end, the inventors have developed a method for detecting and/or quantifying integration of recombinant vector nucleic acids encoding a transgene, such as a CAR, but not the residual plasmid that was used to deliver the transgene or unintegrated recombinant vector nucleic acid sequence. The ability to identify whether a vector has successfully incorporated into a cell with a transgene-independent sequence allows for more accurate, universal, and cheaper quantitation using quantitative PCR, digital PCR, or other quantitative methods. The present disclosure provides methods and kits that utilize the change in the 5'-LTR upon integration into a host genome, versus the sequence of the 5'-LTR in the transfer plasmid vector, to identify and quantitate genetic information delivered and incorporated via a recombinant vector. Such information, including the copy number, is critical to understanding and optimizing the conditions for transfection or transduction. The methods of the invention facilitate monitoring transduction efficiency of lentivirus vectors, and in vivo characterization. Accordingly the present disclosure provides improved methods for quantitating recombinant vector nucleic acid integration into a target cell's genome. Although the exemplary embodiments described herein relate to detection of integrated retroviral vector nucleic acids, the methods of the invention may be applied to any recombinant nucleic acid vector sequence that upon integration into a host genome is distinguishable from unintegrated nucleic acid.

Throughout this application, various documents are referenced. Disclosures of these documents in their entireties are hereby incorporated by reference into this application.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, cell and cancer biology, virology, immunology, microbiology, genetics and protein and nucleic acid chemistry described herein are those well known and commonly used in the art. Each embodiment of the inventions described herein may be taken alone or in combination with one or more other embodiments of the inventions.

The methods and techniques of the present invention are generally performed according to conventional methods well known in the art and as described in various general and more specific references that are cited and discussed throughout the present specification, unless otherwise indicated. The methods and techniques of the various embodiments are generally performed, unless otherwise indicated, according to methods of molecular biology, cell biology, biochemistry, microarray and sequencing technology well known in the art and as described in various general and more specific references that are cited and discussed throughout this specification. See, e.g. Motulsky, "Intuitive Biostatistics", Oxford University Press, Inc. (1995); Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2003); Harlow and Lane, Antibodies: A Laboratory Manual, Cold Spring Harbor Laboratory Press, Cold Spring Harbor, N.Y. (1990); Coffin et al., Retroviruses, Cold Spring Harbor Laboratory Press; Cold Spring Harbor, N.Y. (1997); Bast et al., Cancer Medicine, 5th ed., Frei, Emil, editors, BC Decker Inc., Hamilton, Canada (2000); Lodish et al., Molecular Cell Biology, 4th ed., W. H. Freeman & Co., New York (2000); Griffiths et al., Introduction to Genetic Analysis, 7th ed., W. H. Freeman & Co., New York (1999); Gilbert et al., Developmental Biology, 6th ed., Sinauer Associates, Inc., Sunderland, MA (2000); and Cooper, The Cell A Molecular Approach, 2nd ed., Sinauer Associates, Inc., Sunderland, MA (2000).

Chemistry terms used herein are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

Definitions

The terms "polynucleotide", "nucleic acid" and "nucleic acid molecules", as used herein, are used interchangeably. They refer to a polymeric form of nucleotides of any length, DNA molecules (e.g., cDNA or genomic DNA), RNA molecules (e.g., mRNA), DNA-RNA hybrids, and analogs thereof. The nucleic acid molecule can be a nucleotide, oligonucleotide, double-stranded DNA, single-stranded DNA, multi-stranded DNA, complementary DNA, genomic DNA, non-coding DNA, messenger RNA (mRNAs), microRNA (miRNAs), small nucleolar RNA (snoRNAs), ribosomal RNA (rRNA), transfer RNA (tRNA), small interfering RNA (siRNA), heterogeneous nuclear RNAs (hnRNA), or small hairpin RNA (shRNA). In certain embodiments, the methods can be performed on a nucleic acid sample such as DNA or RNA, e.g., genomic DNA.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified, such as by conjugation with a labeling component. The term "recombinant" polynucleotide means a polynucleotide of genomic, cDNA, semi synthetic, or synthetic origin which either does not occur in nature or is linked to another polynucleotide in a non natural arrangement. The polynucleotide may be operatively linked to an "expression control sequence," which refers to a nucleotide sequence that regulates the expression of a gene.

The term "endogenous" refers to a protein, a nucleic acid, a cell, or another molecule that originates from a source inside a subject.

The term "exogenous" refers to a protein, a nucleic acid, a cell, or another molecule that originates from a source outside of a subject. Non limiting examples of exogenous molecules include: a recombinant protein, a plasmid, a virus, a cell from a donor subject, a tissue from a donor subject, an organ from a donor subject, or a synthetic chemical.

Throughout this specification, the word "comprise" or variations such as "comprises" or "comprising" will be understood to imply the inclusion of a stated integer or group of integers but not the exclusion of any other integer or group of integers.

The singular forms "a," "an," and "the" include plural reference unless the context clearly dictates otherwise.

The term "including" is used to mean "including but not limited to". "Including" and "including but not limited to" are used interchangeably.

A "subject", or "individual" are used interchangeably and refer to any animal, such as a dog, a cat, a bird, livestock, and particularly a mammal, and preferably a human.

The term "recombinant vector nucleic acid" refers to a nucleic acid sequence that comprises a vector for delivering a nucleic acid that includes at least one modification compared to a naturally occurring sequence and may contain a transgene that encodes an exogenous protein to be expressed in the genome of transduced cells.

The term "retroviral vector nucleic acid" refers to a nucleic acid sequence that is at least a portion of a retroviral vector that includes at least one modification to a naturally occurring retroviral sequence and may contain a transgene that encodes an exogenous protein to be expressed in the genome of transduced cells, e.g., a portion of a lentiviral vector transfer plasmid. "Retroviral vector nucleic acid sequence" does not include naturally occurring retroviral nucleic acid that is not associated with a retroviral vector. Retroviral vector nucleic acid that has been integrated into a host cell genome is sometimes referred to as "proviral nucleic acid."

The term "retroviral vector" refers to a vector containing structural and functional genetic elements that are primarily derived from a retrovirus.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (MoMLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV), Rous Sarcoma Virus (RSV) and lentivirus.

The term "lentiviral vector" is a subset of retroviral vectors that refers to a vector containing structural and functional genetic elements that are primarily derived from a lentivirus. In certain embodiments, lentiviral vectors are produced according to known methods. See e.g., Kutner et al, BMC Biotechnol. 2009; Kutner et al., Nat. Protoc. 2009. The present invention includes recombinant, retroviral and lentiviral vector constructs expressing a transgene that can be directly transduced into a cell. In particular embodiments, a lentiviral vector is used to deliver a polynucleotide encoding a CAR to a cell.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al, (1996a, 1996b, and 1998); Zufferey et al, (1997); Dull et al, 1998, U.S. Pat. Nos. 6,013,516; and 5,994,136, many of which may be adapted to produce a viral vector or transfer plasmid contemplated herein.

"Lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which causes immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

Lentiviral vectors preferably contain several safety enhancements as a result of modifying the LTRs. "Self-inactivating" (SIN) vectors refers to replication-defective vectors. The term "self-inactivating vector" refers to vectors in which the right (3') LTR enhancer-promoter region, known as the U3 region, has been modified (e.g., by deletion or substitution) to prevent viral transcription beyond the first round of viral replication. In certain embodiments, the LTR U3 is a ΔU3. Consequently, the vectors are capable of infecting and then integrating into the host genome only once, and can not be passed further. This is because the right (3') LTR U3 region is used as a template for the left (5') LTR U3 region during viral replication and, thus, the viral transcript can not be made without the U3 enhancer-promoter. If the viral transcript is not made, it can not be processed or packaged into virions, hence the life cycle of the virus ends. Accordingly, SIN vectors greatly reduce risk of creating unwanted replication-competent virus since the right (3') LTR U3 region has been modified to prevent viral transcription beyond the first round of replication, hence eliminating the ability of the virus to be passed. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The term "long terminal repeat (LTR)" refers to domains of base pairs located at the ends of certain recombinant DNAs, such as retroviruses, which, in their natural sequence context, are direct repeats and contain U3, R and U5 regions. LTRs generally provide functions fundamental to the expression of recombinant genes (e.g., promotion, initiation and polyadenylation of gene transcripts) and to viral replication.

The term "R region" refers to the region within recombinant LTRs beginning at the start of the capping group (i.e., the start of transcription) and ending immediately prior to the start of the poly A tract. The R region is also defined as being flanked by the U3 and U5 regions. The R region plays an important role during reverse transcription in permitting the transfer of nascent DNA from one end of the genome to the other. The term "PBS region" refers to the region downstream of the U5 region of the 5'-LTR which serves as a primer binding site (PBS) for the tRNA$^{Lys}$ primer, and is required for initiation of reverse transcription.

The term "specifically hybridizes to an integrated recombinant vector nucleic acid" refers to specific hybridization of a nucleic acid, e.g., a primer, to a recombinant vector nucleic acid that has integrated into a host cell's genome, but not to the residual plasmid that was used to deliver the transgene or unintegrated recombinant vector nucleic acid sequence.

Assays for Testing

The efficacy and properties of recombinant vector nucleic acids of the disclosure may be readily tested by utilizing any of a number of available in vitro or in vivo assays. A few such assays are described below. The disclosure contemplates that any recombinant vector nucleic acids of the disclosure may be tested using any of these assays, as well as others known in the art.

In some embodiments, quantitative Polymerase Chain Reaction (qPCR) is employed in order to quantify recombinant vector nucleic acid integration into a target cell's genome. In some embodiments, digital Polymerase Chain Reaction (dPCR) is employed in order to quantify recombinant vector nucleic acid integration into a target cell's genome. In some embodiments, droplet digital Polymerase Chain Reaction (ddPCR) is employed in order to quantify recombinant vector nucleic acid integration into a target cell's genome. In these embodiments, cultures of cells (e.g., PBMC cells) expressing the recombinant vector nucleic acid are harvested and prepared for qPCR or dPCR using primers specific to an LTR sequence of the integrated recombinant vector nucleic acid. Such experiments detect the integrated recombinant vector nucleic acid sequence encoding the CAR in the genome of transduced CAR-T cells, but not the residual non-integrated transfer plasmid.

Methods and Uses of the Disclosure

The present disclosure provides methods of detecting and/or quantifying integration of a recombinant vector nucleic acid into a cellular genome. In this method, in certain embodiments, one provides a biological sample comprising a host cellular genome. Providing a biological material includes providing fresh biological material, such as biological material taken at a given time for the purpose of this analysis. Providing a biological material also includes using previously obtained biological material taken at another point during patient care for this or for other purposes, or using archived patient material. Biological material may be freshly obtained or previously obtained, and where previously obtained, may have been stored prior to use (e.g., at room temperature, refrigerated, or frozen). Exemplary biological materials include, but are not limited to, whole blood, serum, plasma, urine, feces, cerebrospinal fluid, ascites, and the like.

In some embodiments, the biological material may be purified or otherwise processed to isolate genomic DNA of the biological sample. Such processing may include HPLC, exclusion chromatography, gel electrophoresis, affinity chromatography, commercial DNA extraction or purification kit, or other purification technique.

Methods of amplifying genomic DNA of the biological sample include, but are not limited to, polymerase chain reactions (PCRs), linear polymerase reactions, nucleic acid sequence-based amplification (NASBAs), rolling circle amplifications, digital PCR (dPCR), droplet digital PCR (ddPCR), end point PCR, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like.

In certain embodiments, one then amplifies genomic DNA of the biological sample using a quantitative amplification technique. Quantitative amplification techniques are known to those of skill in the art and include quantitative PCR (qPCR), digital PCR and end point PCR. "qPCR" or "real-time quantitative PCR" (real-time quantitative polymerase chain reaction) refers to an experimental method of using PCR to amplify and quantify target nucleic acid at the same time. Quantification is performed using a plurality of measuring chemical substances (including, for instance, fluorescent dye of SYBR™ green or fluorescent reporter oligonucleotide probe of Taqman probe), and real-time quantification is performed with the amplified DNA accumulated in the reaction after every amplification cycle. For a description of digital PCR methods, see, e.g., Hindson et al. (2011) Anal. Chem. 83(22):8604-8610; Pohl and Shih (2004) Expert Rev. Mol. Diagn. 4(1):41-47; Pekin et al. (2011) Lab Chip 11 (13): 2156-2166; Pinheiro et al. (2012) Anal. Chem. 84 (2): 1003-1011; Day et al. (2013) Methods 59(1):101-107; herein incorporated by reference in their entireties.

As used herein, the term "primer" means an oligonucleotide which can act as a starting point for synthesis under a condition of inducing the synthesis of a primer extension product complementary to a nucleic acid chain (template), that is, in the presence of a polymerization mixture comprising a nucleotide and a DNA polymerase, and suitable temperature and pH conditions. In certain embodiments, the primer is a deoxyribonucleotide and is a single strand. The primers used in the present invention may include naturally occurring dNMPs (i.e., dAMP, dGMP, dCMP, and dTMP), modified nucleotides or non-natural nucleotides. In addition, the primer may also include ribonucleotides.

The primer should be long enough to be able to prime the synthesis of the extension product in the presence of the polymerization mixture. The suitable length of the primer is determined by a number of factors, such as a temperature, an application, and a source of the primer, while being typically 15-30 nucleotides. Short primer molecules generally require lower temperatures to form a sufficiently stable hybrid complex with the template.

In some embodiments, a detectable nucleic acid probe that specifically hybridizes to an amplification product (e.g., an integrated retroviral nucleic acid amplicon or a control nucleic acid amplicon) generates a signal that is detectable in an amplification reaction. In some embodiments, the detectable nucleic acid probe comprises a detectable agent. In some embodiments, the detectable nucleic acid probe comprises a quencher. The detectable agent and quencher are as disclosed in US Patent Publication No. 20190284610, which is hereby incorporated by reference.

In certain embodiments, fluorescence analysis can be performed by a commercial detector (for example, Droplet Reader from biorad), and the droplet fluorescence signal of each sample can be detected in the apparatus, and the number of positive and negative droplets can be counted, and the analysis can be completed automatically.

In certain embodiments, the term "detectable nucleic acid probe" means a TaqMan probe used for quantitative PCR. In certain embodiments, a fluorescent material (HEX, VIC, FAM dye) is attached to the probe. In certain embodiments, 31ABkFQ may be used as a quencher on the 3' side of the probe. The TaqMan probe is an oligonucleotide tagged with a fluorescent substance at the 5' end and a quencher substance at the 3' end, respectively. The TaqMan probe specifically hybridizes to template DNA in an annealing step, but does not exhibit fluorescence even when light is applied, because there is a quencher at the 3' end of the probe. In the following extension step, the 5' to 3' exonuclease activity of Taq DNA polymerase degrades the TaqMan probe hybridized to the template. Then, the fluorescent substance is separated from the probe and the inhibition by the quencher is released. Through such a principle the fluorescence due to PCR reaction is quantitatively shown.

In certain embodiments, a fluorescence quenching assay may be used wherein a probe according to the invention comprises a fluorophore and a quencher that are positioned such that in the absence of a target nucleic acid, and at temperatures below the Tm of the probe there is quenching of the fluorescence. A wide range of fluorophores may be used in probes and primers according to this invention. Available fluorophores include coumarin, fluorescein (FAM), tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges. Suitable quenchers described in the art include 31ABkFQ, DABCYL and variants thereof, such as DAB-SYL, DABMI and Methyl Red. Fluorophores can also be used as quenchers, because they tend to quench fluorescence when in the vicinity of certain other fluorophores. In some embodiments, a preferred quencher is 31ABkFQ. In some embodiments, a preferred fluorophore is fluorescein (FAM). In some embodiments, a preferred internal quencher is ZEN. In some embodiments, a preferred fluorophore is VIC.

In certain embodiments, one simultaneously amplifies genomic DNA of the biological sample with quantitative PCR using at least one pair of oligonucleotide primers that specifically amplify a reference polynucleotide sequence and using a primer pair comprising a first oligonucleotide primer and a second oligonucleotide primer, wherein at least one oligonucleotide primer of the primer pair specifically hybridizes to an integrated retroviral vector polynucleotide sequence. Specifically, as shown in FIG. 1B, a reference polynucleotide sequence can be used to determine the number of cells present in the sample with genomic information and thus allow for estimation of the copy number. This may improve the accuracy of prior methods, which commonly used conversion factors from the mass of genetic material in a sample to determine copy number. As also shown in FIG. 1B, a retroviral vector sequence including a CAR encoding polynucleotide may be incorporated into the genome of the host cell. This incorporated retroviral vector sequence notably includes a 5'-LTR delta U3 region that is not present in the unincorporated vector, as shown in FIG. 1A. The method, by including a primer complementary to only the 5'-LTR delta U3 region in FIG. 1B, is thus selective for only the integrated retroviral vector sequence and not for unintegrated retroviral vectors.

In some embodiments, the retroviral vector nucleic acid is based on a member of the genus lentivirus. Specifically, lentiviruses have shown strong transfection efficiency and are a proven tool for incorporating genetic information into a host cell. In some embodiments, the lentivirus is human immunodeficiency virus 1 (HIV-1), or human immunodeficiency virus 2 (HIV-2). In some embodiments, a primer for amplifying the integrated retroviral vector nucleic acid specifically hybridizes to an LTR sequence of the integrated retroviral vector sequence. In some embodiments, a primer for amplifying the retroviral vector nucleic acid specifically hybridizes to the U3 region of the 5'LTR of the lentivirus. In some embodiments, a primer for amplifying the retroviral vector nucleic acid specifically hybridizes to the U3 region and R region of the 5'LTR of the lentivirus. In some embodiments, a primer for amplifying the retroviral vector nucleic acid specifically hybridizes to the PBS region of the 5'LTR of the lentivirus. In some embodiments, a primer for amplifying the retroviral vector nucleic acid specifically hybridizes to the PBS region and R region of the 5'LTR of the lentivirus. In some embodiments, a primer for amplifying the retroviral vector nucleic acid specifically hybridizes to the psi (Ψ) packaging signal. In some embodiments, the sequence that is specific to an incorporated retroviral vector nucleic acid comprises the nucleic acid sequence of SEQ ID NO:1, SEQ ID NO: 5 or SEQ ID NO: 14. In some embodiments, the sequence that is specific to an incorporated retroviral vector nucleic acid comprises the nucleic acid sequence of SEQ ID NO:2, SEQ ID NO: 6, or SEQ ID NO: 15. In some embodiments, one uses a detectable nucleic acid probe that specifically hybridizes to the amplified retroviral vector nucleic acid. Specifically, in some embodiments, the probe that specifically hybridizes to the retroviral vector nucleic acid comprises the nucleic acid sequence of SEQ ID NO: 3, SEQ ID NO: 4, SEQ ID NO: 7, or SEQ ID NO: 16. In some embodiments, the probe that specifically hybridizes to the retroviral vector nucleic acid comprising the nucleic acid sequence of SEQ ID NO: 3, SEQ ID NO: 4, SEQ ID NO: 7, or SEQ ID NO: 16 further comprises a fluorophore or quencher at the 5' end, 3' end, and/or between the ninth and tenth nucleotide of the probe measured from the 5' end of the sequence. In some embodiments, the probe that specifically hybridizes to the retroviral vector nucleic acid consists of the nucleic acid sequence of SEQ ID NO: 3, SEQ ID NO: 4, SEQ ID NO: 7, or SEQ ID NO: 16 including a fluorophore or quencher at the 5' end, 3' end, and/or internal. In specific embodiments, an internal quencher is between the ninth and tenth nucleotide of the probe measured from the 5' end of the sequence. In some embodiments, a probe has a fluorophore at the 5' end, an internal quencher, and a second quencher at the 3' end. In some embodiments, a preferred quencher is 31ABkFQ. In some embodiments, a preferred fluorophore is fluorescein (FAM). In some embodiments, a preferred internal quencher is ZEN. In some embodiments, a preferred fluorophore is VIC. In some embodiments, the probe that specifically hybridizes to the retroviral vector nucleic acid is /FAM/CTTTCAAGT/ZEN/CCCTGTTCGGGCGCC/31ABkFQ/(SEQ ID NO: 12) or /56-FAM/TGCCTTGAG/ZEN/TGCTT-CAAGTAGTGTGT/3IABkFQ/(SEQ ID NO: 17). In some embodiments, the primer that amplifies a reference sequence present in all host cells comprises a nucleic acid sequence specifically hybridizes to a portion of a sequence encoding a housekeeping protein. Specifically, in some embodiments, the housekeeping protein is albumin. In some embodiments, the primer sequence that specifically hybridizes a portion of the albumin gene is SEQ ID NO: 8 and/or 9. In some embodiments, the sequence of the probe that specifically hybridizes to the albumin nucleic acid is SEQ ID NO: 10. In some embodiments, the probe that specifically hybridizes to the albumin nucleic acid is /5HEX/AGGGAGA/ZEN/GAT-TTGTGTGGGCATGAC/3IABkFQ/ (SEQ ID NO: 11).

In this method, in certain embodiments, one then detects and/or quantifies the genomic nucleic acid that was amplified, where the ratio of amplified retroviral vector nucleic acid to reference nucleic acid is correlated with the number of copies of the retroviral vector nucleic acid integrated in the cellular genome. Specifically, as discussed above, because one primer is specific to a polynucleotide sequence that only appears if the retroviral vector is incorporated into the host cell genome, the number of sequences counted by qPCR is directly proportional to the number of integrated retroviral vectors in the sample. Division by the number of reference polynucleotide sequences detected allows for direct computation of the copy number for a given biological sample.

In certain embodiments, the disclosure provides methods for determining the integrated retroviral vector nucleic acid copy number in a genome of a subject. In some embodiments of the method, one provides a biological sample containing genomic DNA of the subject. In some embodiments of the method, one amplifies a portion of the integrated retroviral vector nucleic acid and a reference polynucleotide sequence in the genome of the subject in the biological sample by quantitative PCR. In some embodiments of the method, one determines (i) the amount of amplified polynucleotide containing the retroviral vector nucleic acid sequence and (ii) the amount of amplified polynucleotide containing the reference polynucleotide sequence and determining the ratio of (i) to (ii), wherein the ratio corresponds with the integrated retroviral vector nucleic acid copy number.

In some embodiments, the amplification comprises combining the sample with a composition comprising a primer pair specific for the integrated retroviral vector nucleic acid sequence, and conducting quantitative PCR. In some embodiments, the amplification comprises combining the sample with a composition comprising a primer pair specific for the integrated retroviral vector nucleic acid sequence, and conducting a quantitative amplification technique. In some embodiments, the amplification further comprises a primer pair specific for the reference polynucleotide sequence, and conducting a quantitative amplification technique, wherein the integrated retroviral vector nucleic acid sequence and reference polynucleotide are separately amplified in substantially equal proportion. In some embodiments, one primer of the primer pair for the integrated retroviral vector nucleic acid sequence specifically hybridizes to the 5'LTR. In some embodiments, one primer of the primer pair for amplifying the retroviral vector nucleic acid specifically hybridizes to the U3 region of the 5'LTR. In some embodiments, one primer of the primer pair for the integrated retroviral vector nucleic acid sequence specifically hybridizes to the U3 region and R region of the 5'LTR. In some embodiments, one primer of the primer pair for amplifying the retroviral vector nucleic acid specifically hybridizes to the PBS region of the 5'LTR. In some embodiments, the integrated retroviral vector nucleic acid sequence comprises a transgene. In some embodiments, the transgene encodes a chimeric antigen receptor (CAR), which specifically binds a certain target antigen.

The present disclosure provides yet another method for monitoring transduction efficiency of a retroviral vector. In some embodiments, one provides one or more biological samples containing genomic DNA transduced by a retroviral vector nucleic acid, wherein a portion of the retroviral vector nucleic acid is integrated into the genomic DNA. In some embodiments, one determines the integrated retroviral vector sequence copy number in the genomic DNA of each biological sample according to the methods described herein. In some embodiments, one compares the retroviral vector sequence copy numbers of the biological sample to a reference.

The present disclosure also provides a method of lot release testing for a cell product transduced by a retroviral vector. In some embodiments, one provides one or more biological samples of the cell product containing genomic DNA transduced by a retroviral vector from each lot. In some embodiments, one determines the integrated retroviral vector sequence copy number in each biological sample according to the methods of the disclosure. In some embodiments, one compares the retroviral vector sequence copy numbers of the biological samples to a reference. In some embodiments, lots where the integrated retroviral vector sequence copy numbers passes predetermined criteria are released. In certain embodiments, predetermined criteria may be a copy number range or percent variation from a control.

The present disclosure also provides assay acceptance criteria and sample acceptance criteria that may be used to determine the validity of an assay or sample, respectively, for quantifying the integration of a recombinant vector nucleic acid. In some embodiments, the integration of the recombinant vector nucleic acid sequence is determined by calculating a vector copy number per cell (VCN/cell) value, defined as twice the ratio of the measured quantities of provirus and the reference polynucleotide sequence. In some embodiments, the quantities of provirus or reference polynucleotide sequence are determined via quantitative PCR (qPCR). In some embodiments, the quantities of provirus or reference polynucleotide sequence are determined via quantitative PCR (qPCR) from the threshold cycle (Ct) measured by a qPCR instrument. The threshold cycle (Ct) is defined as the number of PCR cycles needed to reach a set fluorescent threshold from each amplification curve for either the provirus or the reference polynucleotide sequence and is reciprocally proportional to the content of the respective polynucleotide sequence.

In some embodiments, the one or more of the assay acceptance criteria or sample acceptance criteria utilize three or more replicates of three or more standard samples. In some embodiments, the three or more standard samples, each at or about 3.20 VCN/cell, are prepared from a predetermined base standard sample by up to four 5-fold serial dilutions using buffer as diluent. In some embodiments, the base standard sample contains 121,212.121 copies of the provirus and 75,757.576 copies of the reference polynucleotide sequence. In some embodiments, one or more of the assay acceptance criteria or sample acceptance criteria require, for three or more replicates of one or more positive control samples, comparison of the measured quantity of the provirus and reference polynucleotide sequence with the nominal quantities of the provirus and reference polynucleotide sequence calculated during preparation of said one or more positive control samples from separate samples of known concentration of provirus and reference polynucleotide sequence.

In some embodiments, the method further comprises evaluating the validity of an assay for quantifying the integration of a recombinant vector nucleic acid sample by assessing one or more assay acceptance criteria. In some embodiments, the assay is valid if it meets one or more of, or all of, the assay acceptance criteria selected from the group consisting of: (a) the threshold cycle of both the provirus and the reference polynucleotide sequence in all the replicates of a control containing no template DNA is undeterminable; (b) the correlation coefficient for the standard curves of both the provirus and the reference polynucleotide sequence, generated by linear regression using the standard samples, is greater than or equal to 0.90, 0.91, 0.92, 0.93, 0.94, 0.95, 0.96 or 0.97; (c) the estimated VCN/cell value from the slope of said standard curves indicates a PCR efficiency of between 80% and 120%, between 82% and 118%, between 84% and 116%, between 86% and 114%, between 88% and 116%, or between 90% and 110%; (d) the threshold cycle of both the provirus and the reference polynucleotide sequence in none of the replicates of any of the standard samples is undeterminable; (e) the mean threshold cycle of both the provirus and the reference polynucleotide sequence in the base standard sample is less than or equal to 30.0, 28.0, 26.0, 24.0, or 22.0; (f) the standard deviation in the threshold cycle of both the provirus and the reference polynucleotide sequence in each standard sample is less than or equal to 0.95, 0.90, 0.85, 0.80, 0.75, 0.70, 0.65, or 0.60; (g) the average measured copies of the reference polynucleotide sequence for the one or more positive control samples is within 50%, 45%, 40%, 35%, or 30% of the nominal expected value, (h) the measured mean VCN/cell value for the one or more positive control samples is within 50%, 45%, 40%, 35%, or 30% of the nominal expected VCN/cell value for each control; and (i) the coefficient of variation of the VCN/cell value for the one or more positive control samples is less than or equal to 50%, 45%, 40%, 35%, 30%, 25%, or 20%.

In some embodiments, the method further comprises evaluating the validity of the quantification of the integration of a recombinant vector nucleic acid for a sample by assessing one or more sample acceptance criteria. In some embodiments, a sample is valid if it meets one or more of, or all of, the sample acceptance criteria selected from the group consisting of: (a) the average copy value of the reference polynucleotide sequence in the sample is within 50%, 45%, 40%, 35%, or 30% of the expected value of 30,303.030 copies; (b) if the sample has a genomic DNA (gDNA) concentration less than 0.02 μg/μL, the expected copies of the reference polynucleotide sequence for that sample is calculated from the amount of DNA actually loaded into the reactions; (c) the mean target provirus copy value in the sample is between the validated range of the copy value for the assay; (d) the mean target provirus copy value in the sample is between 121,212.121 and 193.939 copies; (e) the coefficient of variation of the VCN/cell value for the replicates of the target sample is less than or equal to 50%, 45%, 40%, 35%, 30%, 25%, or 20%; and (f) the standard deviation in the cycle threshold of both the target provirus and the target reference polynucleotide sequence in the sample is less than or equal to 0.95, 0.90, 0.85, 0.80, 0.75, 0.70, 0.65, or 0.60.

In some embodiments, the method of quantifying integration of a recombinant vector nucleic acid into a cellular genome further comprises a method for identification of the transgene. In some embodiments, the method for identification of the transgene comprises: (a) providing a biological sample comprising a host cellular genome; (b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to the transgene; and (c) detecting and/or quantifying the genomic nucleic acid that was amplified through step (b). In some embodiments, the transgene encodes a chimeric antigen receptor. In some embodiments, the chimeric antigen receptor comprises the amino acid sequence of SEQ ID NO: 18, SEQ ID NO: 20, or SEQ ID NO: 22. In some embodiments, the chimeric antigen receptor is a polypepide encoded by a nucleic acid sequence comprising the sequence of SEQ ID NO: 19 or SEQ ID NO: 21. In some embodiments, the chimeric antigen receptor recognizes BCMA, KLK2 or GPRC5D.

Kits

In certain embodiments, the disclosure also provides a kit for measuring integrated recombinant vector sequence copy number. In certain embodiments, a kit may comprise one or more primers of the disclosure. In certain embodiments, a kit may comprise one or more probes of the disclosure.

The present disclosure also provides a kit for measuring integrated recombinant vector sequence copy number. In some embodiments, the kit includes one primer or both primers of a primer pair that specifically hybridizes to an integrated recombinant vector nucleic acid, wherein the primer pair specifically amplifies a portion of the integrated recombinant vector nucleic acid. In some embodiments, the kit includes a detectable nucleic acid probe that specifically hybridizes to the amplified recombinant vector nucleic acid.

The present disclosure also provides another kit for measuring integrated recombinant vector sequence copy number. In some embodiments, the kit includes a forward primer that specifically hybridizes to an integrated recombinant vector nucleic acid. In some embodiments, the kit includes a forward primer that specifically hybridizes to an integrated recombinant vector nucleic acid, wherein the forward primer comprises the nucleic acid sequence of SEQ ID NO: 1, SEQ ID NO: 5, or SEQ ID NO: 14. In some embodiments, the kit includes a reverse primer that specifically hybridizes to an integrated recombinant vector nucleic acid. In some embodiments, the kit includes a reverse primer that specifically hybridizes to an integrated recombinant vector nucleic acid, wherein the reverse primer comprises the nucleic acid sequence of SEQ ID NO: 2, SEQ ID NO: 6, or SEQ ID NO: 15. In some embodiments, the kit includes a detectable probe. In some embodiments, the kit includes a detectable probe comprising the nucleic acid sequence of SEQ ID NO: 3, SEQ ID NO: 4, SEQ ID NO: 7, or SEQ ID NO: 16.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1: Materials and Methods for Examples

Transient transfection experiments were performed with Lipofectamine2000 (Life Technologies) and plasmid in a cell density of $4 \times 10^5$ per well of a 6-well plate. Medium was removed after 24 hours and replaced with fresh growth medium.

A qPCR assay was performed to determine the copy number of transfected cells. First, standards and quality controls were separately prepared for both reference gene and 5'-LTR sequence linearized plasmids in the presence of tRNA (yeast tRNA; Invitrogen cat #657491). Second, we prepared the reference gene master mix, which consists of: Forward primer (SEQ ID NO: 8), Reverse primer (SEQ ID NO: 9), Probe /5HEX/AGGGAGA/ZEN/GAT-TTGTGTGGGCATGAC/3IABkFQ/ (SEQ ID NO: 11) in 1× Fast Advanced Master Mix (ThermoScientific cat #4444558). Third, we prepared the 5'-LTR master mix which consists of: Forward primer (SEQ ID NO: 5), Reverse primer (SEQ ID NO: 6), and Probe /FAM/CTTTCAAGT/ZEN/CCCTGTTCGGGCGCC/31ABkFQ/(SEQ ID NO: 12) in 1× Fast Advanced Master Mix (ThermoScientific cat #4444558).

The qPCR assay was prepared by adding MasterMix, standard, QCs and samples to a multi-well plate. The qPCR assay was run on any real time PCR instrument. The qPCR assay includes, but is not limited to preparation by adding MasterMix, standard, QCs and samples to a 96 well plate. The qPCR assay may be run on, but is not limited to, a Quantstudio instrument with conditions: 50° C. 2 min, 95° C. 10 min, 95° C. 15 sec for melting, 60° C. 1 min for annealing and extension.

Example 2: Quantitation of CAR Encoding Polynucleotide Incorporation in T-Cells Delivered by HIV-1

A Universal qPCR assay detecting only the integrated retroviral vector sequence encoding any transgene in the genome of transduced cell products, but not the transfer plasmid that was used to generate the lentiviral vectors. Based on the unique characteristics of the lentiviral vector integration into a host genome, a specific qPCR assay was developed that can quantify the copy number of the lentiviral transduced cells, but not unintegrated vector (see FIGS. 1A and 1B).

The retroviral vector nucleic acid that is integrated in a cellular genome is readily quantifiable using the methods of the invention.

Primer and probe sets 1-5 (according to Table 1) were used to amplify integrated lentiviral vector sequences according to the methods of Example 1. The primer sets 1-4 amplified lentiviral sequences from cell samples where the vector was integrated and did not amplify in control cell samples where transduction was not performed but lentiviral transfer plasmid was present (see FIG. 2). The control (Set 5) amplified the human albumin (hALB) sequence in all samples with cells.

Example 3: Quantitation of the Integrated GPRc5d CAR-T in Blood

The methods described in the previous Examples were used to quantify the integrated CAR transgene copy number in mouse studies using a GPRc5d CAR-T. This study was conducted to pick the final clone/construct.

Figure 3A:
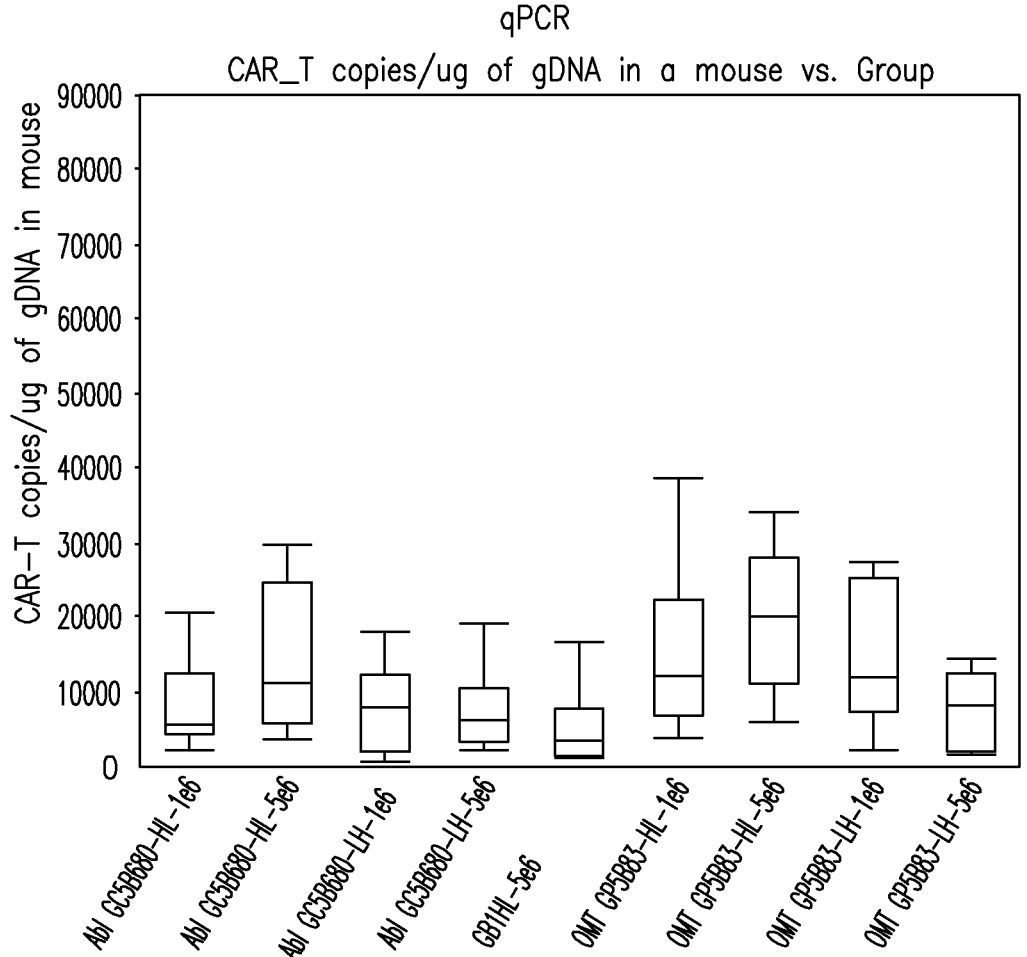
FIGS. 3A-3B show side-by-side qPCR (3A) vs flow cytometry (3B) GPRc5d CAR-T quantitation results in blood.
Figure 3B:
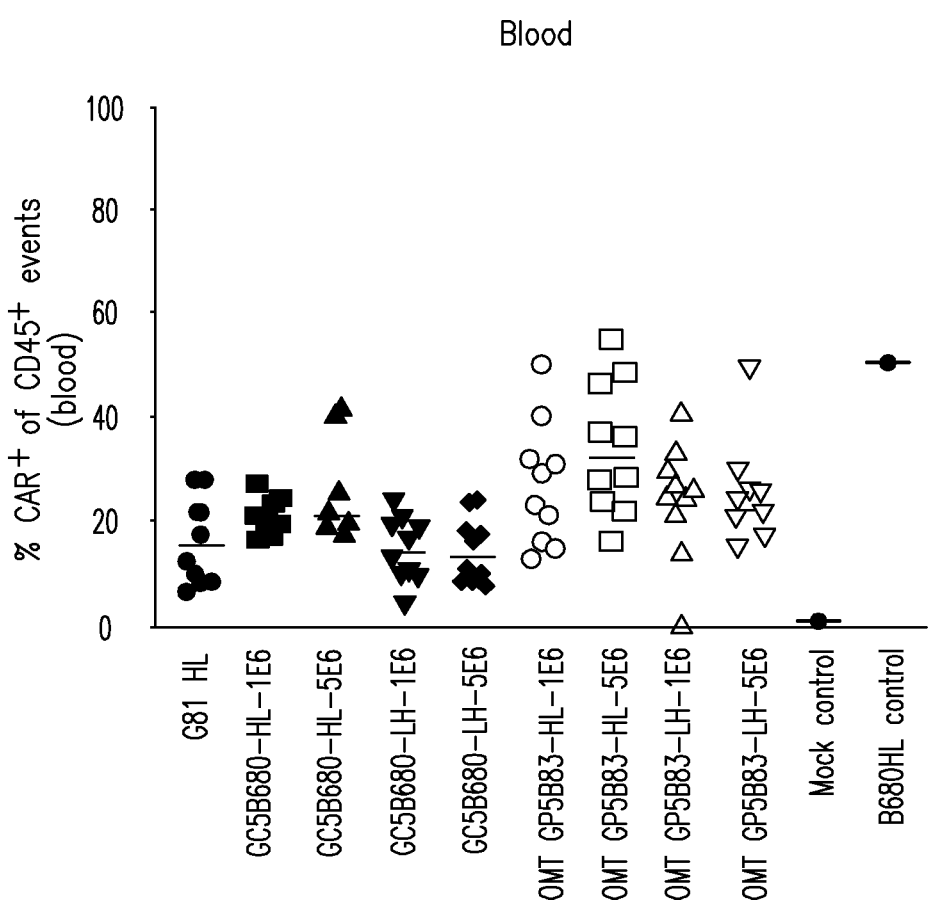

The qPCR assay was developed and successfully used in five different mouse studies. In the GPRc5d CAR-T study, the provirus method copy number correlates with flow data (FIG. 3A-3B). 5LTR pair 3 (set 3 according to Table 1) was used in these experiments.

Example 4: Quantitation of the Integrated Transgene in a CAR-T Product

A quantitative real time PCR (qPCR) assay for the quantitation of the integrated transgene was developed by targeting the cellular genome integrated form of the HIV derived lentivirus 5' LTR region (provirus sequence target region) in a CAR-T product. The exemplary CAR-T product, which recognizes the target antigen BCMA, has the amino acid sequence of SEQ ID NO: 18. The assay is a singleplex or multiplex qPCR where the integrated 5'LTR region of the provirus sequence as well as human albumin (hALB; reference housekeeping gene) were targeted. This method may be used but is not limited to pre-formulated frozen CAR-T cell pellets for the determination of transduction efficiency reported as vector copy number (VCN) per cell.

Genomic DNA (gDNA) was extracted from pre-formulated CAR-T cell pellets using the Purelink gDNA Isolation Kit. Pre-formulated cell pellets were stored frozen at ≤−60° C. prior to DNA isolation. The isolated DNA was either stored at ≤−60° C. and thawed at a later time for quantification or immediately quantified using the Qubit 4 Fluorometer and the fluorescence-based Qubit dsDNA Broad Range assay kit. The Qubit 4 Fluorometer was calibrated using the two Standards supplied in the Qubit dsDNA Broad Range kit. The Standards were prepared and run with each set of DNA samples to be quantitated. The Standards and DNA sample reactions were prepared using the same Qubit working solution. Following quantitation, the isolated DNA was diluted to a working concentration of 0.020 μg/μL.

The qPCR reaction was prepared using an oligonucleotide mixture (containing provirus primer and probe set 4 including /56-FAM/TGCCTTGAG/ZEN/TGCTT- CAAGTAGTGTGT/3IABkFQ/(SEQ ID NO: 17) and hALB primer and probe set 5, according to Table 1) and qPCR TaqPath ProAmp Master Mix solution, diluted using molecular grade water. The final concentration of each of the three oligonucleotides in the provirus primer and probe set was 200 nM. The final concentration of each of the hALB forward and reverse primers was 50 nM, while that of the hALB probe was 200 nM.

Provirus Standard #1 was made by spiking 0.05 μg/μL of PBMC DNA with linear 5' LTR plasmid so that 5 μL of Standard #1 contained 121,212.121 copies of plasmid. Standard #1 was serially diluted using buffer. The Provirus qPCR Mid Control was made by spiking 0.02 μg/μL of PBMC gDNA with linear 5' LTR plasmid such that 5 μL of the Mid Control contained 30,303.030 copies of 5' LTR plasmid. The Provirus qPCR Low Control was made by diluting the Mid Control volume 1:10 using 0.02 μg/μL PBMC gDNA as the diluent. This equated to nominal vector copy numbers of 2.00 VCN/cell in 5 μL of the Mid Control and 0.20 VCN/cell in 5 μL of the Low Control, but the actual VCN/cell value for each lot of Mid Control and Low Control was determined during reagent qualification.

The master mix was loaded in designated wells of a qPCR plate. Three replicates of each diluted standard point, Provirus Mid Control, Provirus Low Control, test article DNA and low EDTA TE buffer (i.e., the no template control or NTC) were each loaded into designated wells containing master mix in the qPCR plate. The qPCR plate was loaded into a real time PCR instrument to execute the qPCR reaction.

The measured threshold cycle (Ct) for each target (provirus and hALB), was determined by the qPCR instrument. The Ct and log concentration values for the Standards were used to generate the standard curve by linear regression. The standard curve was used to calculate the copies of each target for each control and test article replicate.

The VCN/cell was calculated for each Sample, the Mid Control and the Low Control replicates as follows.

$$VCN/\text{cell} = \left(\frac{\text{Transgene Quantity}}{hALB\ \text{Quantity}}\right) * 2$$

Where x is each value from the population, x̄ is the mean of the data set, and N is the size of the population, the mean, standard deviation and % CV for the triplicate VCN/cell values for each Sample, Mid and Low Control was then calculated as:

$$SD = \sqrt{\left(\frac{\sum (x - \bar{x})^2}{N - 1}\right)}.$$

The following assay acceptance criteria were used to yield a valid assay:

The correlation coefficient ($R^2$) value for both the Provirus and hALB standard curves must have been ≥0.97.

The slope of the standard curve must have been between −3.585 and −3.104 (equating to a PCR efficiency of 90.08-109.97%)

All Ct replicates of the NTC must have be "Undetermined" for both the Provirus and hALB targets.

The mean Ct for Standard #1 must have been ≤22.0 for the Provirus and hALB targets, and none of the Ct replicates for any of the Standards could have been "Undetermined."

The Ct SD for each Standard must have been ≤0.60 for both the Provirus and hALB targets.

The average hALB copies for both the Mid and Low Controls must have been 30,303.030 copies±30% (expected range: 21,212.121-39,393.939 copies).

The mean VCN/cell result for the Mid Control and Low Control must have been ≥−30% and ≤+30% of the qualified VCN/cell value for each control.

The % CV of the VCN/cell for the Mid and Low Control replicates must have been ≤20%.

Any sample that did not meet all the following acceptance criteria were deemed invalid:

The Ct SD for each sample must have been ≤0.60 for both the Provirus and hALB targets. The Ct SD was not accessed on samples determined to be below or above the assay range.

The average hALB copies for each sample must have been 30,303.030 copies±30% (expected range: 21,212.121 to 39,393.939 copies).

If the concentration of the sample gDNA was <0.02 μg/μL, the expected copies of hALB for that sample from the amount of DNA actually loaded into the reactions was calculated.

The mean Provirus target copy value for each sample must have been equal to or between the validated range of the assay to calculate the VCN/cell result.

If the mean Provirus copy value for a sample was >121, 212.121, the sample was considered above the assay range.

If the mean Provirus copy value for a sample was <193.939 copies, the sample was considered below the assay range.

The % CV of the sample VCN/cell replicates must have been ≤20%. The % CV was not accessed on samples determined to be below or above the assay range or for samples that failed hALB acceptance criteria.

The Ct SD for each sample must have been ≤0.60 for both, the Provirus and hALB targets. The % CV was not accessed on samples determined to be below or above the assay range or for samples that failed hALB acceptance criteria.

For any samples that met all sample acceptance criteria, the transduction efficiency was reported as the average VCN/cell result, accurate to 2 decimal places.

BCMA CAR-T production tested using the present methods showed a lower integrated copy number than an assay targeting the vector packaging signal (PSI) that cannot differentiate integrated vs. unintegrated copy number. Results confirm the PSI method was potentially picking up plasmid contamination (Table 2) in the tested BCMA CAR-T batch.

The method was also used for other CAR-T products such as exemplary GPRc5d and KLK2 CAR-T products in development. The amino acid sequences of the CARs comprise SEQ ID NOs: 20 and 22, respectively. A comparison of these results with the PSI method did not show any difference in VCN between the methods (Table 3). The results confirm there was no plasmid contamination in the GPRc5d CAR-T and KLK2 CAR-T batch production processes.

Example 5: Quantitation of the Integrated Transgene in Other CAR-T Products

The quantitative real time PCR (qPCR) assay for the quantitation of the integrated transgene is also useful in other CAR-T products, such as those targeting GPRC5D. The method of Example 3 was used to determine the CAR-T cellular kinetics in mouse studies as the average VCN/cell or transgene copies/μg gDNA in mouse blood for a GPRc5d CAR-T product.

Example 6: Identification of Transgene after Quantitation of the Integrated Transgene in CAR-T Products Although the provirus qPCR method is useful to accurately estimate the VCN/cell in batches of a cellular genome integrated with a CAR-T transgene sequence, a qPCR method using primers that specifically hybridize to nucleotide sequences within the transgene is still useful to confirm the identity of the CAR transgene. This is because the provirus qPCR method is universal and not transgene-specific.

The design and execution of a transgene qPCR method is the same as that of the provirus qPCR method, differing only in the sequence, and optionally the concentration, of the forward primer, the reverse primer and the probe sequences for the transgene target. In the case that the transgene target encoded the CAR in the BCMA CAR-T product, which recognizes the target antigen BCMA, comprises the amino acid sequence of SEQ ID NO: 18, and is encoded by a nucleic acid sequence comprising of SEQ ID NO: 19, we used a primer/probe set specific for the CD137 (4-1BB) and CD3ζ derived sequences of the CAR transgene. We used a concentration of 100 nM for each of the transgene forward and reverse primers. The human albumin (hALB) housekeeping gene oligonucleotides were the same for both methods, but the concentration of the hALB forward and reverse primers in the transgene method was 75 nM.

Briefly, to execute the transgene qPCR method, standard curves were generated for both transfer plasmid and human albumin (hALB) using a 5-point serial dilution of a mock transduced lymphocyte cell line. Genomic DNA isolated from post-harvest samples was analyzed in triplicate. The copies of both transgene and hALB for each triplicate DNA sample was interpolated from the respective standard curves. The average copies of hALB were used to estimate the number of cells the sample DNA was derived from. The average copies of transgene present in the sample DNA was divided by the estimated number of cells the sample DNA was derived from to determine the vector copy number per cell of the sample.

TABLE 1

| | | Sequences | |
|---|---|---|---|
| Set # | Primer/ Probe | Sequence | SEQ ID NO: |
| 1 | 5LTR Pair 1 F Primer | CTAATTCACTCCCAACGAAGACAAG | 1 |
| | 5LTR Pair 1 R Primer | GGTTTCCCTTTCGCTTTCAAG | 2 |
| | 5LTR Pair 1 Probe | CGCCACTGCTAGAGAT | 3 |
| 2 | 5LTR Pair 2 F Primer | CTAATTCACTCCCAACGAAGACAAG | 1 |

TABLE 1-continued

Sequences

Figure 2:
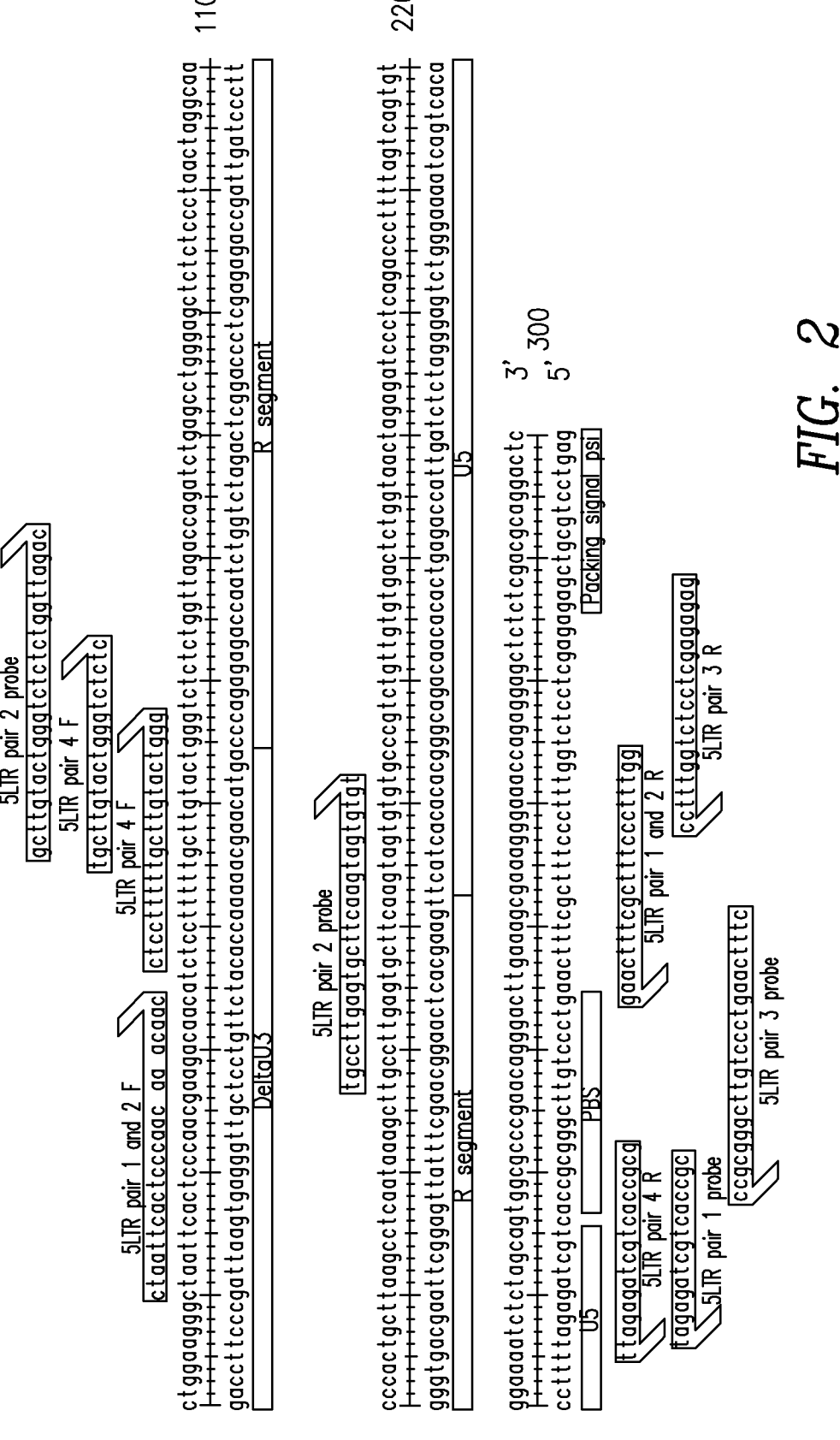
FIG. 2 shows an alignment of selected primers and probes of the disclosure against an exemplary lentiviral vector sequence. The following sequences are depicted: Example lentiviral vector sequence (SEQ ID NO: 13); 5LTR_Pair 1 and 2_F Primer (SEQ ID NO: 1); 5LTR_Pair 1 Probe (SEQ ID NO: 3); 5LTR_Pair 1 and 2_R Primer (SEQ ID NO: 2); 5LTR_Pair 2_Probe (SEQ ID NO: 4); 5LTR_Pair 3_F Primer (SEQ ID NO: 5); 5LTR_Pair 3_Probe (SEQ ID NO: 7); 5LTR_Pair 3_R Primer (SEQ ID NO: 6), 5LTR_Pair 4_F Primer (SEQ ID NO: 14); 5LTR_Pair 4_R Primer (SEQ ID NO: 15); 5LTR_Pair 4_Probe (SEQ ID NO: 16).

| Set # | Primer/ Probe | Sequence | SEQ ID NO: |
|---|---|---|---|
| | 5LTR Pair 2 R Primer | GGTTTCCCTTTCGCTTTCAAG | 2 |
| | 5LTR Pair 2 Probe | GCTTGTACTGGGTCTCTCTGGTTAGAC | 4 |
| 3 | 5LTR Pair 3 F Primer | CTGCTTTTTGCTTGTACTGGG | 5 |
| | 5LTR Pair 3 R Primer | GAGAGAGCTCCTCTGGTTTCC | 6 |
| | 5LTR Pair 3 Probe | CTTTCAAGTCCCTGTTCGGGCGCC | 7 |
| | Labeled 5LTR Pair 3 Probe | /FAM/CTTTCAAGT/ZEN/CCCTGTTCGGGCGCC /31ABkFQ/ | 12 |
| 4 | 5LTR Pair 4 F Primer | TGCTTGTACTGGGTCTCTC | 14 |
| | 5LTR Pair 4 R Primer | GCGCCACTGCTAGAGATT | 15 |
| | 5 LTR Pair 4 Probe | TGCCTTGAGTGCTTCAAGTAGTGTGT | 16 |
| | Labeled 5LTR Pair 4 Probe | /56-FAM/TGCCTTGAG/ZEN/TGCTTCAAGTAGTGT GT/3IABkFQ/ | 17 |
| 5 | Albumin F Primer | TCATCTCTTGTGGGCTGTAATC | 8 |
| | Albumin R Primer | TGCTGGTTCTCTTTCACTGAC | 9 |
| | Albumin Probe | AGGGAGAGATTTGTGTGGGCATGAC | 10 |
| | Labeled Albumin Probe | /5HEX/AGGGAGA/ZEN/GATTTGTGTGGGCAT GAC/3IABkFQ/ | 11 |
| | Portion of lenti-viral vector sequence targeted in FIG. 2 | CTGGAAGGGCTAATTCACTCCCAACGAAGAC AAGATCTGCTTTTTGCTTGTACTGGGTCTCTC TGGTTAGACCAGATCTGAGCCTGGGAGCTCT CTGGCTAACTAGGGAACCCACTGCTTAAGCC TCAATAAAGCTTGCCTTGAGTGCTTCAAGTA GTGTGTGCCCGTCTGTTGTGTGACTCTGGTAA CTAGAGATCCCTCAGACCCTTTTAGTCAGTG TGGAAAATCTCTAGCAGTGGCGCCCGAACAG GGACTTGAAAGCGAAAGGGAAACCAGAGGA GCTCTCTCGACGCAGGACTC | 13 |
| | Exem-plary BCMA CAR Trans-gene (amino acid sequence) | MALPVTALLLPLALLLHAARPQVKLEESGGGL VQAGRSLRLSCAASEHTFSSHVMGWFRQAPG KERESVAVIGWRDISTSYADSVKGRFTISRDNA KKTLYLQMNSLKPEDTAVYYCAARRIDAADF DSWGQGTQVTVSSGGGGSEVQLVESGGGLVQ AGGSLRLSCAASGRTFTMGWFRQAPGKEREFV AAISLSPTLAYYAESVKGRFTISRDNAKNTVVL QMNSLKPEDTALYYCAADRKSVMSIRPDYWG | 18 |

TABLE 1-continued

Sequences

| Set # | Primer/ Probe | Sequence | SEQ ID NO: |
|---|---|---|---|
| | se-quence) | QGTQVTVSSTSTTTPAPRPPTPAPTIASQPLSLR PEACRPAAGGAVHTRGLDFACDIYIWAPLAGT CGVLLLSLVITLYCKRGRKKLLYIFKQPFMRPV QTTQEEDGCSCRFPEEEEGGCELRVKFSRSADA PAYQQGQNQLYNELNLGRREEYDVLDKRRGR DPEMGGKPRRKNPQEGLYNELQKDKMAEAYS EIGMKGERRRGKGHDGLYQGLSTATKDTYDA LHMQALPPR | |
| | Exem-plary BCMA CAR Trans-gene of (nu-cleic acid se-quence) | ATGGCTCTGCCCGTCACCGCTCTGCTGCTGCC TCTGGCTCTGCTGCTGCACGCTGCTCGCCCTC AGGTCAAACTGGAAGAATCTGGCGGAGGCC TGGTGCAGGCAGGACGGAGCCTGCGCCTGA GCTGCGCAGCATCCGAGCACACCTTCAGCTC CCACGTGATGGGCTGGTTTCGGCAGGCCCCA GGCAAGGAGAGAGAGAGCGTGGCCGTGATC GGCTGGAGGGACATCTCCACATCTTACGCCG ATTCCGTGAAGGGCCGGTTCACCATCAGCCG GGACAACGCCAAGAAGACACTGTATCTGCA GATGAACAGCCTGAAGCCCGAGGACACCGC CGTGTACTATTGCGCAGCAAGGAGAATCGAC GCAGCAGACTTTGATTCCTGGGGCCAGGGCA CCCAGGTGACAGTGTCTAGCGGAGGAGGAG GATCTGAGGTGCAGCTGGTGGAGAGCGGAG GCGGCCTGGTGCAGGCCGGAGGCTCTCTGAG GCTGAGCTGTGCAGCATCCGGAAGAACCTTC ACAATGGGCTGGTTTAGGCAGGCACCAGGA AAGGAGAGGGAGTTCGTGGCAGCAATCAGC CTGTCCCCTACCCTGGCCTACTATGCCGAGA GCGTGAAGGGCAGGTTTACCATCTCCCGCGA TAACGCCAAGAATACAGTGGTGCTGCAGATG AACTCCCTGAAACCTGAGGACACAGCCCTGT ACTATTGTGCCGCCGATCGGAAGAGCGTGAT GAGCATTAGACCAGACTATTGGGGGCAGGG AACACAGGTGACCGTGAGCAGCACTAGTACC ACGACGCCAGCGCCGCGACCACCAACACCG GCGCCCACCATCGCGTCGCAGCCCCTGTCCC TGCGCCCAGAGGCGTGCCGGCCAGCGGCGG GGGGCGCAGTGCACACGAGGGGGCTGGACT TCGCCTGTGATATCTACATCTGGGCGCCCTTG GCCGGGACTTGTGGGGTCCTTCTCCTGTCACT GGTTATCACCCTTTACTGCAAACGGGGCAGA AAGAAACTCCTGTATATATTCAAACAACCAT TTATGAGACCAGTACAAACTACTCAAGAGGA AGATGGCTGTAGCTGCCGATTTCCAGAAGAA GAAGAAGGAGGATGTGAACTGAGAGTGAAG TTCAGCAGGAGCGCAGACGCCCCCGCGTACC AGCAGGGCCAGAACCAGCTCTATAACGAGCT CAATCTAGGACGAAGAGAGGAGTACGATGT TTTGGACAAGAGACGTGGCCGGGACCCTGAG ATGGGGGGAAAGCCGAGAAGGAAGAACCCT CAGGAAGGCCTGTACAATGAACTGCAGAAA GATAAGATGGCGGAGGCCTACAGTGAGATT GGGATGAAAGGCGAGCGCCGGAGGGGCAAG GGGCACGATGGCCTTTACCAGGGTCTCAGTA CAGCCACCAAGGACACCTACGACGCCCTTCA CATGCAGGCCCTGCCCCCTCGCTAA | 19 |
| | Exem-plary GPRC5D CAR Trans-gene (amino acid se-quence) | DIVMTQTPLSSPVTLGQPASISCRSSQSLVHSDG NTYLSWLQQRPGQPPRLLIYKISNRFFGVPDRF SGSGAGTDFTLKISRVEAEDVGVYYCMQATQF PHTFGQGTKLEIKGGSEGKSSGSGSESKSTGGS QVTLKESGPVLVKPTETLTLTCTVSGFSLTNIR MSVSWIRQPPGKALEWLAHIFSNDEKSYSSSLK SRLTISRDTSKSQVVLTLTNVDPVDTATYYCAR MRLPYGMDVWGQGTTVTVSSTSTPAPRPPTPA PTIASQPLSLRPEACRPAAGGAVHTRGLDFACD IYIWAPLAGTCGVLLLSLVITLYCKRGRKKLLY IFKQPFMRPVQTTQEEDGCSCRFPEEEEGGCEL RVKFSRSADAPAYKQGQNQLYNELNLGRREE YDVLDKRRGRDPEMGGKPRRKNPQEGLYNEL QKDKMAEAYSEIGMKGERRRGKGHDGLYQGL STATKDTYDALHMQALPPR | 20 |

TABLE 1-continued

Sequences

| Set # | Primer/ Probe | Sequence | SEQ ID NO: |
|---|---|---|---|
| Exemplary GPRC5D CAR Transgene (nucleic acid sequence) | | ATGGCTTGGGTGTGGACCTTGCTATTCCTGAT GGCAGCTGCCCAAAGTATACAGGCCGACATT GTGATGACCCAAACACCTCTTAGTAGTCCTG TAACTCTCGGACAGCCAGCTTCAATATCTTG TCGCTCAAGTCAATCCCTCGTCCATTCCGAC GGCAACACCTACCTCTCTTGGCTCCAACAGA GACCCGGCCAGCCTCCCAGACTTCTCATCTA CAAAATCAGTAACAGGTTCTTCGGCGTCCCT GACAGGTTCAGTGGATCTGGAGCAGGTACAG ATTTCACCTTGAAGATAAGTAGAGTGGAGGC TGAGGACGTAGGCGTCTATTATTGTATGCAA GCTACCCAATTCCCACATACATTCGGCCAAG GCACTAAATTGGAAATAAAAGGCGGCTCCG AGGGCAAGAGCAGCGGCAGCGGCAGCGAGA GCAAGAGCACCGGCGGCAGCCAAGTAACAC TCAAGGAGAGCGGACCAGTCTTGGTGAAACC AACTGAGACCTTGACTTTGACATGTACTGTA AGTGGCTTCAGCCTTACCAACATCAGGATGT CAGTATCTTGGATAAGGCAACCACCTGGCAA GGCACTCGAATGGCTGGCACACATCTTTTCT AACGACGAAAAATCCTATTCTTCCAGTCTCA AAAGTCGCCTTACCATCAGCCGAGATACCAG TAAGAGTCAAGTAGTTCTTACATTGACCAAT GTAGATCCAGTTGATACAGCCACATACTACT GCGCACGAATGCGGCTTCCATACGGCATGGA TGTATGGGACAGGGAACTACTGTTACCGTT AGTTCCACTAGTACCCCAGCCCCACGCCCTC CCACCCCTGCTCCTACAATAGCATCCCAGCC CTTGTCACTTCGCCCCGAAGCATGCAGACCA GCCGCAGGCGGTGCTGTGCATACCCGAGGAC TGGACTTCGCCTGCGACATCTACATCTGGGC CCCACTGGCCGGCACCTGCGGCGTGCTGCTG CTGAGCCTGGTGATCACCCTGTACTGCAAGC GCGGCCGCAAGAAGCTGCTGTACATCTTCAA GCAGCCATTCATGCGCCCAGTGCAGACCACC CAGGAGGAGGACGGCTGCAGCTGCCGCTTCC CAGAGGAGGAGGAGGGCGGCTGCGAGCTGC GCGTGAAGTTCAGCCGCAGCGCCGACGCCCC AGCCTACAAGCAGGGCCAGAACCAGCTGTA CAACGAGCTGAACCTGGGCCGCCGCGAGGA GTACGACGTGCTGGACAAGCGCCGCGGCCGC GACCCAGAGATGGGCGGCAAGCCACGCCGC AAGAACCCACAGGAGGGCCTGTACAACGAG CTGCAGAAGGACAAGATGGCCGAGGCCTAC AGCGAGATCGGCATGAAGGGCGAGCGCCGC CGCGGCAAGGGCCACGACGGCCTGTACCAG GGCCTGAGCACCGCCACCAAGGACACCTACG ACGCCCTGCACATGCAGGCCCTGCCACCACG CTGA | 21 |
| Exemplary KLK2 CAR Transgene (amino acid sequence) | | EIVLTQSPSFLSASVGDRVTITCRASQGISSYLS WYQQKPGKAPKLLIYATSTLQSGVPSRFSGSGS GTEFTLTISSLQPEDFATYYCQQLNSYPRTFGQ GTKVEIKGGSEGKSSGSGSESKSTGGSEVQLVE SGGGLVQPGGSLRLSCAASGFTFSSYWMTWV RQAPGKGLEWVANIKQDGSERYYVDSVKGRF TISRDNAKNSLYLQMNSLRAEDTAVYYCARD QNYDILTGHYGMDVWGQGTTVTVSSTSTPAPR PPTPAPTIASQPLSLRPEACRPAAGGAVHTRGL DFACDIYIWAPLAGTCGVLLLSLVITLYCKRGR KKLLYIFKQPFMRPVQTTQEEDGCSCRFPEEEE GGCELRVKFSRSADAPAYKQGQNQLYNELNL GRREEYDVLDKRRGRDPEMGGKPRRKNPQEG LYNELQKDKMAEAYSEIGMKGERRRGKGHDG LYQGLSTATKDTYDALHMQALPPR | 22 |

TABLE 2

BCMA CAR-T production tested using the present methods showed a lower integrated copy number than an assay targeting the vector packaging signal (PSI) that cannot differentiate integrated vs. unintegrated copy number

| Sample | Attempt 1(5LTR) VCN/cell | Attempt (5LTR) VCN/cell | BioTD PSI VCN/cell |
|---|---|---|---|
| Sample 1: 20020993 MAL CAR TEC150587_0819_3_D1 Day 10_D1_MC | 0.19 | 0.22 | 0.65 |
| Sample 2: 20012638 TEC150587_819_3_D1 Day 10 D1_M3 | 0.38 | 0.48 | 1.70 |
| Jurkat BCMA gDNA LM-RP3-01078 18 Jul. 2019 | N/A | 1.30 | ~1.0 |

TABLE 3

Comparison of VCN of CAR T products targeting KLK2 and GPRC5D using the present methods and PSI method

| | Sample Name | PSI qPCR Avg VCN/cell | 5LTR qPCR AvgVCN/cell |
|---|---|---|---|
| 1 | 5D20-10: 25e6 Day 1 Activation 48 hr | 0.36 | 0.34 |
| 2 | 5D20-12: 3e6/cm2 IL2 D6 | 1.03 | 0.88 |
| 3 | 5D20-12: 3e6/cm2 IL2 D3 & D6 | 1.00 | 0.95 |
| 4 | 5D20-12: 6e6/cm2 IL2 D6 | 0.93 | 0.85 |
| 5 | 5D20-12: 6e6/cm2 IL2 D3 & D6 | 0.88 | 0.84 |
| 6 | 5D20-13: 5e6 Day 8 Harvest | 0.35 | 0.28 |
| 7 | 5D20-13: 5e6 Day 9 Harvest | 0.47 | 0.37 |
| 8 | 5D20-13: 7.5e6 Day 8 Harvest | 0.36 | 0.29 |
| 9 | 5D20-13: 7.5e6 Day 9 Harvest | 0.40 | 0.39 |
| 10 | SH20-KLK2-001 post Harvest CAR-T pellet 2e6 15 Jan. 2020 | 0.29 | 0.25 |
| 11 | SH20-KLK2-001 post Harvest MOCK pellet 2e6 15 Jan. 2020 | 0.00 | N/A |
| 12 | SH20-KLK2-002 post Harvest CAR-T pellet 2e6 22 Jan. 2020 | 0.36 | 0.34 |
| 13 | SH20-KLK2-002 post Harvest MOCK pellet 2e6 22 Jan. 2020 | 0.00 | N/A |
| 14 | SH20-KLK2-004 post Harvest CAR-T pellet 2e6 12 Feb. 2020 | 0.39 | 0.34 |
| 15 | SH20-KLK2-004 post Harvest MOCK pellet 2e6 12 Feb. 2020 | 0.00 | N/A |

REFERENCES

1. Sadelain M, Brentjens R, Riviere I (2013) The Basic Principles of Chimerica Antigen Receptor (CAR) Design. Cancer Discov 3(4): 388-398.
2. Titov A, Valiullina A, Zmievskaya E, Zaikova E, Petukhov A, Miftakhova R, Bulatov E, Rizvamov (2020) Advancing CAR T-Cell Therapy for Solid Tumors: Lessons Learned from Lymphoma Treatment. Cancer 12: 125-146.
3. Charrier S, Ferrand M, Zerbato M, Precigout G, Viornery A, Bucher-Laurent S, Benkheilifa-Ziyyat S, Merten O W, Perea J, Galy A (2011) Quantification of Lentiviral Vector Copy Numbers in Individual Hematopoietic Colony-Forming Cells Shows Vector Dose-Dependent Effects on the Frequency and Level of Transduction. Gene Therapy 18: 479-487.
4. Lizee G, Aerts J L, Gonzales M I, Chinnasamy N, Morgan R A, Topalian S L (2003) Real-Time Quantitative Reverse Transcriptase-Polymerase Chain Reaction As A Method For Determining Lentiviral Vector Titers And Measuring Transgene Expression. Hum Gene Ther. 14(6): 497-507.

5. Siegel R, Naishadham D, Jemal A (2012) Cancer statistics, 2012. CA: a cancer journal for clinicians 62: 10-29.

Particular embodiments of the invention are set forth in the following numbered paragraphs:

1. A method for quantifying integration of a recombinant vector nucleic acid into a cellular genome, the method comprising:
   (a) providing a biological sample comprising a host cellular genome;
   (b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to an integrated recombinant vector polynucleotide sequence; and
   (c) detecting and/or quantifying the genomic nucleic acid that was amplified through step (b).

2. The method according to paragraph 1, wherein the recombinant vector contains a transgene.

3. The method according to paragraph 2, wherein the transgene encodes a chimeric antigen receptor.

4. The method according to any one of paragraphs 1-3, wherein the recombinant vector is a gene therapy vector.

5. The method according to paragraph 4, wherein the gene therapy vector is a viral vector.

6. The method according to any one of paragraphs 1-5, wherein the biological sample is a cell sample or a tissue sample.

7. The method according to paragraph 6, wherein the tissue sample is blood, plasma, serum, saliva or a tissue biopsy.

8. The method according to any one of paragraphs 1-7, wherein the sample is from a subject.

9. The method according to paragraph 8, wherein the subject is a human.

10. The method according to any one of paragraphs 1-9, wherein the recombinant vector is a retroviral vector.

11. The method according to paragraph 10, wherein the retroviral vector is a lentiviral vector.

12. The method according to paragraph 11, wherein the lentivirus that the lentiviral vector is based on is human immunodeficiency virus 1 (HIV-1), or human immunodeficiency virus 2 (HIV-2).

13. The method according to any one of paragraphs 1-12, wherein the oligonucleotide primer that specifically hybridizes to an integrated recombinant vector polynucleotide sequence specifically hybridizes to an LTR sequence of the integrated recombinant vector sequence.

14. The method according to any one of paragraphs 1-13, wherein the oligonucleotide primer that specifically hybridizes to an integrated recombinant vector polynucleotide sequence in step (b) comprises the nucleic acid sequence of SEQ ID NO:1, SEQ ID NO: 5, or SEQ ID NO: 14.

15. The method according to paragraph 14, wherein the second oligonucleotide primer for amplifying the recombinant vector nucleic acid used in step (b) comprises the nucleic acid sequence of SEQ ID NO:2, SEQ ID NO: 6, or SEQ ID NO: 15.

16. The method according to paragraph 11, wherein the oligonucleotide primer that specifically hybridizes to an integrated lentiviral vector polynucleotide sequence used in step (b) specifically hybridizes to the U3 region of the 5'LTR of the lentiviral vector nucleic acid sequence.

17. The method according to paragraph 11, wherein the oligonucleotide primer that specifically hybridizes to an integrated lentiviral vector polynucleotide sequence used in step (b) specifically hybridizes to the U3 region and R region of the 5'LTR of the lentiviral vector nucleic acid sequence.

18. The method according to paragraph 11, wherein the oligonucleotide primer that specifically hybridizes to an integrated lentiviral vector polynucleotide sequence used in step (b) specifically hybridizes to the PBS region of the 5'LTR of the lentiviral vector nucleic acid sequence.

19. The method according to paragraph 11, wherein the oligonucleotide primer that specifically hybridizes to an integrated lentiviral vector polynucleotide sequence used in step (b) specifically hybridizes to the psi (T) packaging signal.

20. The method according to any one of paragraphs 1-19, wherein the quantitative amplification technique is qPCR.

21. The method according to any one of paragraphs 1-19, wherein the quantitative amplification technique is dPCR or ddPCR.

22. The method according to any one of paragraphs 1-19, wherein the quantitative amplification technique is end point PCR.

23. The method according to any one of paragraphs 1-22, wherein step (b) utilizes a detectable nucleic acid probe that specifically hybridizes to the amplified recombinant vector nucleic acid.

24. The method according to paragraph 23, wherein the recombinant vector nucleic acid is a lentiviral vector.

25. The method according to either paragraph 23 or paragraph 24, wherein the probe for the integrated recombinant vector nucleic acid specifically hybridizes to an LTR sequence of the integrated recombinant vector sequence.

26. The method according to paragraph 24, wherein the probe for the lentiviral vector nucleic acid used in step (b) specifically hybridizes to the U3 region and R region of the 5'LTR of the lentiviral vector nucleic acid sequence.

27. The method according to paragraph 24, wherein the probe for the lentiviral vector nucleic acid used in step (b) specifically hybridizes to the U5 region and PBS region of the 5'LTR of the lentiviral vector nucleic acid sequence.

28. The method according to paragraph 24, wherein the probe for the lentiviral vector nucleic acid used in step (b) specifically hybridizes to the PBS region of the 5'LTR of the lentiviral vector nucleic acid sequence 29. The method according to paragraph 24, wherein the probe for the lentiviral vector nucleic acid used in step (b) specifically hybridizes to the R region and U5 region of the 5'LTR of the lentiviral vector nucleic acid sequence.

30. The method according to any one of paragraphs 23-25, wherein the probe that specifically hybridizes to the recombinant vector nucleic acid comprises the nucleic acid sequence of SEQ ID NO: 3, SEQ ID NO: 4, SEQ ID NO: 7, or SEQ ID NO: 16.

31. A method for monitoring transduction efficiency of a recombinant vector nucleic acid, comprising, a) providing one or more biological samples containing genomic DNA transduced by a recombinant vector nucleic acid, wherein a portion of the recombinant vector nucleic acid is integrated into the genomic DNA; and b) quantifying the recombinant vector nucleic acid integrated in the host cellular genome according to the method of any one of paragraphs 1-30.

32. The method according to any one of paragraphs 1-30, wherein step (c) further comprises comparing the integrated recombinant vector sequence copy numbers of the biological sample to a reference polynucleotide sequence.

33. The method according to paragraph 32, wherein the reference polynucleotide sequence encodes a housekeeping protein.

34. The method according to paragraph 33, wherein the housekeeping protein is human albumin.

35. The method according to any one of paragraphs 1-34, further comprising at least one pair of oligonucleotide primers that specifically amplify a reference polynucleotide sequence.

36. The method according to paragraph 31, further comprising comparing the integrated recombinant vector sequence copy numbers of the biological sample to a reference.

37. A method of lot release testing for a cell product transduced by a recombinant vector, comprising a) providing one or more biological samples of a cell product containing genomic DNA transduced by a recombinant vector from each lot;

b) quantifying the recombinant vector nucleic acid integrated in the host cellular genome in each biological sample according to the method of any one of paragraphs 1-35;

c) comparing the integrated recombinant vector sequence copy numbers quantified in step (b) for the biological samples to a reference; and d) releasing lots where the integrated recombinant vector sequence copy numbers pass predetermined criteria.

38. A method of quantifying integration of a lentiviral vector nucleic acid into a cellular genome, the method comprising:

(a) providing a biological sample comprising a host cellular genome;

(b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to an integrated lentiviral vector polynucleotide sequence; and (c) quantifying the genomic nucleic acid that was amplified through step (b), wherein quantifying the lentiviral vector nucleic acid integrated in the host cellular genome comprises comparing the ratio of amplified lentiviral vector nucleic acid to a reference, wherein the oligonucleotide primer pair comprise the nucleic acid sequence of SEQ ID NO:1 and the nucleic acid sequence of SEQ ID NO:2, respectively, or the nucleic acid sequence of SEQ ID NO:5 and the nucleic acid sequence of SEQ ID NO:6, respectively, or the nucleic acid sequence of SEQ ID NO:14 and the nucleic acid sequence of SEQ ID NO:15, respectively.

39. The method according to any one of paragraphs 1-38, wherein step (b) utilizes an intercalating dye.

40. The method according to paragraph 39, wherein the intercalating dye is SYBR green.

41. The method according to any one of paragraphs 32-35, wherein the integrated recombinant vector sequence copy number and the reference polynucleotide sequence copy number are measured in multiplex.

42. The method according to any one of paragraphs 32-35, wherein the integrated recombinant vector sequence copy number and the reference polynucleotide sequence copy number are measured in singleplex.

43. The method according to paragraph 3, wherein the chimeric antigen receptor comprises the amino acid sequence of SEQ ID NO: 18, 20 or 22.

44. The method according to paragraph 3, wherein the chimeric antigen receptor recognizes BCMA, KLK2 or GPRC5D.

45. The method according to paragraph 2, further comprising a method for identification of the transgene.

46. The method according to paragraph 45, wherein the method for identification of the transgene comprises:

(a) providing a biological sample comprising a host cellular genome;

(b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to the transgene; and (c) detecting and/or quantifying the genomic nucleic acid that was amplified through step (b).

47. The method according to any one of paragraphs 32-35, wherein the method further comprises evaluating the validity of an assay for quantifying the integration of a recombinant vector nucleic acid by assessing one or more assay acceptance criteria selected from the group consisting of:

(a) the threshold cycle of both the provirus and the reference polynucleotide sequence in all the replicates of a control containing no template DNA is undeterminable;

(b) the correlation coefficient for the standard curves of both the provirus and the reference polynucleotide sequence, generated by linear regression using the standard samples, is greater than or equal to 0.97;

(c) the estimated copy values for provirus and reference polynucleotide sequence from the slope of said standard curves indicates a PCR efficiency of between 90% and 110%;

(d) the threshold cycle of both the provirus and the reference polynucleotide sequence in none of the replicates of any of the standard samples is undeterminable;

(e) the mean threshold cycle of both the provirus and the reference polynucleotide sequence in the base standard sample is less than or equal to 22.0;

(f) the standard deviation in the threshold cycle of both the provirus and the reference polynucleotide sequence in each standard sample is less than or equal to 0.60;

(g) the average measured copies of the reference polynucleotide sequence for the one or more positive control samples is within 30% of the nominal expected value;

(h) the measured mean VCN/cell value for the one or more positive control samples is within 30% of the nominal expected VCN/cell value for each control; and (i) the coefficient of variation of the VCN/cell value for the one or more positive control samples is less than or equal to 20%.

48. The method according to any one of paragraphs 32-35, wherein the method further comprises evaluating the validity of the quantification of the integration of a recombinant vector nucleic acid for a sample by assessing one or more sample acceptance criteria selected from the group consisting of:

(a) the average copy value of the reference polynucleotide sequence in the sample is within 30% of the expected value of 30,303.030 copies;

(b) if the sample has a genomic DNA (gDNA) concentration less than 0.02 µg/µL, the expected copies of the reference polynucleotide sequence for that sample is calculated from the amount of DNA actually loaded into the reactions;

(c) the mean target provirus copy value in the sample is between the validated range of the copy value for the assay;

(d) the mean target provirus copy value in the sample is between 121,212.121 and 193.939 copies;

(e) the coefficient of variation of the VCN/cell value for the replicates of the target sample is less than or equal to 20%; and (f) the standard deviation in the cycle threshold of both the target provirus and the target reference polynucleotide sequence in the sample is less than or equal to 0.60.

49. The method according to paragraphs 43 or 44, wherein the chimeric antigen receptor is a polypeptide encoded by a nucleic acid sequence comprising the sequence of SEQ ID NO: 19 or 21.

50. The method according to paragraphs 45 or 46, wherein the transgene is a polypeptide encoded by a nucleic acid sequence comprising the sequence of SEQ ID NO: 19 or 21.

51. An oligonucleotide comprising the nucleic acid sequence of SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 14, SEQ ID NO: 15, or SEQ ID NO: 16.

52. A kit for measuring integrated recombinant vector nucleic acid sequence copy number, comprising:

a primer of a primer pair that specifically hybridizes to an integrated recombinant vector nucleic acid, wherein the primer pair specifically amplifies a portion of the integrated recombinant vector nucleic acid; and a detectable nucleic acid probe that specifically hybridizes to the amplified recombinant vector nucleic acid.

53. A kit for measuring integrated recombinant vector nucleic acid sequence copy number, comprising:

a forward primer that specifically hybridizes to an integrated recombinant vector nucleic acid comprising the nucleic acid sequence of SEQ ID NO:1, SEQ ID NO: 5, or SEQ ID NO: 14;

a reverse primer that specifically hybridizes to an integrated recombinant vector nucleic acid comprising the nucleic acid sequence of SEQ ID NO: 2, SEQ ID NO: 6, or SEQ ID NO: 15, and a detectable probe comprising the nucleic acid sequence of SEQ ID NO: 3, SEQ ID NO: 4, SEQ ID NO: 7, or SEQ ID NO: 16.

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A method for quantifying integration of a recombinant vector nucleic acid into a cellular genome, the method comprising:

(a) providing a biological sample comprising a host cellular genome;

(b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to an integrated recombinant vector polynucleotide sequence; and (c) detecting and/or quantifying the genomic nucleic acid that was amplified through step (b);

wherein the first oligonucleotide primer comprises the nucleic acid sequence of SEQ ID NO: 1, SEQ ID NO: 5, or SEQ ID NO: 14, and wherein the second oligonucleotide primer comprises the nucleic acid sequence of SEQ ID NO: 2, SEQ ID NO: 6, or SEQ ID NO: 15.

2. The method according to claim 1, wherein the recombinant vector contains a transgene.

3. The method according to claim 2, wherein the transgene encodes a chimeric antigen receptor.

4. The method according to claim 1, wherein the recombinant vector is a gene therapy vector.

5. The method according to claim 4, wherein the gene therapy vector is a viral vector.

6. The method according to claim 1, wherein the recombinant vector is a retroviral vector.

7. The method according to claim 6, wherein the retroviral vector is a lentiviral vector.

8. The method according to claim 7, wherein the lentivirus that the lentiviral vector is based on is human immunodeficiency virus 1 (HIV-1), or human immunodeficiency virus 2 (HIV-2).

9. The method according to claim 1, wherein the biological sample is a cell sample or a tissue sample.

10. The method according to claim 9, wherein the tissue sample is blood, plasma, serum, saliva or a tissue biopsy.

11. The method according to claim 1, wherein the oligonucleotide primer that specifically hybridizes to an integrated recombinant vector polynucleotide sequence specifically hybridizes to an LTR sequence of the integrated recombinant vector sequence.

12. The method according to claim 7, wherein the first oligonucleotide primer specifically hybridizes to the U3 region of the 5'LTR of the lentiviral vector nucleic acid sequence.

13. The method according to claim 7, wherein the first oligonucleotide primer specifically hybridizes to the U3 region and R region of the 5'LTR of the lentiviral vector nucleic acid sequence.

14. The method according to claim 7, wherein the second oligonucleotide primer specifically hybridizes to the PBS region located downstream of the U5 region of the 5'LTR of the lentiviral vector nucleic acid sequence.

15. The method according to claim 1, wherein step (c) further comprises comparing the integrated recombinant vector sequence copy numbers of the biological sample to a reference polynucleotide sequence.

16. The method according to claim 1, wherein the quantitative amplification technique is qPCR.

17. The method according to claim 1, wherein the quantitative amplification technique is dPCR or ddPCR.

18. The method according to claim 15, wherein the reference polynucleotide sequence encodes a housekeeping protein.

19. The method according to claim 18, wherein the housekeeping protein is human albumin.

20. The method according to claim 1, wherein step (b) utilizes a detectable nucleic acid probe that specifically hybridizes to the amplified recombinant vector nucleic acid, thereby facilitating detection of the amplified recombinant vector nucleic acid in step (c) of the method.

21. The method according to claim 20, wherein the recombinant vector nucleic acid is a lentiviral vector.

22. The method according to claim 20, wherein the probe that specifically hybridizes to the recombinant vector nucleic acid comprises the nucleic acid sequence of SEQ ID NO: 3, SEQ ID NO: 4, SEQ ID NO: 7, or SEQ ID NO: 16.

23. The method according to claim 20, wherein the probe for the integrated recombinant vector nucleic acid specifically hybridizes to an LTR sequence of the integrated recombinant vector sequence.

24. The method according to claim 21, wherein the probe for the lentiviral vector nucleic acid used in step (b) specifically hybridizes to the U3 region and R region of the 5'LTR of the lentiviral vector nucleic acid sequence.

25. The method according to claim 21, wherein the probe for the lentiviral vector nucleic acid used in step (b) specifically hybridizes to the U5 region and PBS region of the 5'LTR of the lentiviral vector nucleic acid sequence.

26. The method according to claim 21, wherein the probe for the lentiviral vector nucleic acid used in step (b) specifically hybridizes to the PBS region of the 5'LTR of the lentiviral vector nucleic acid sequence.

27. The method according to claim 7, wherein the oligonucleotide primer that specifically hybridizes to an integrated lentiviral vector polynucleotide sequence used in step (b) specifically hybridizes to the psi (Y) packaging signal.

28. The method according to claim 21, wherein the probe for the lentiviral vector nucleic acid used in step (b) specifically hybridizes to the R region and U5 region of the 5'LTR of the lentiviral vector nucleic acid sequence.

29. The method according to claim 1, wherein the biological sample is from a subject.

30. The method according to claim 29, wherein the subject is a human.

31. The method according to claim 1, further comprising at least one pair of oligonucleotide primers that specifically amplify a reference polynucleotide sequence.

32. A method for monitoring transduction efficiency of a recombinant vector nucleic acid, comprising, (a) providing one or more biological samples containing genomic DNA transduced by a recombinant vector nucleic acid, wherein a portion of the recombinant vector nucleic acid is integrated into the genomic DNA; and (b) quantifying the recombinant vector nucleic acid integrated in the host cellular genome according to the method of claim 1.

33. The method according to claim 32, further comprising comparing the integrated recombinant vector sequence copy numbers of the biological sample to a reference.

34. A method of quantifying integration of a lentiviral vector nucleic acid into a cellular genome, the method comprising:

(a) providing a biological sample comprising a host cellular genome;

(b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to an integrated lentiviral vector polynucleotide sequence; and (c) quantifying the genomic nucleic acid that was amplified through step (b), wherein quantifying the lentiviral vector nucleic acid integrated in the host cellular genome comprises comparing the ratio of amplified lentiviral vector nucleic acid to a reference, wherein the oligonucleotide primer pair comprise the nucleic acid sequence of SEQ ID NO: 1 and the nucleic acid sequence of SEQ ID NO:2, respectively, or the nucleic acid sequence of SEQ ID NO:5 and the nucleic acid sequence of SEQ ID NO:6, respectively, or the nucleic acid sequence of SEQ ID NO:14 and the nucleic acid sequence of SEQ ID NO:15, respectively.

35. The method according to claim 3, wherein the chimeric antigen receptor comprises the amino acid sequence of SEQ ID NO: 18, 20 or 22.

36. The method according to claim 3, wherein the chimeric antigen receptor recognizes BCMA, KLK2 or GPRC5D.

37. The method according to claim 1, wherein the quantitative amplification technique is end point PCR.

38. The method according to claim 1, wherein an intercalating dye is used in step (b) to bind to the amplified genomic DNA, facilitating its detection in step (c).

39. The method according to claim 38, wherein the intercalating dye is SYBR green.

40. The method according to claim 15, wherein the integrated recombinant vector sequence copy number and the reference polynucleotide sequence copy number are measured in multiplex.

41. The method according to claim 15, wherein the integrated recombinant vector sequence copy number and the reference polynucleotide sequence copy number are measured in singleplex.

42. The method according to claim 2, further comprising a method for identification of the transgene, wherein the method for identification of the transgene comprises:

(a) providing a biological sample comprising a host cellular genome;

(b) amplifying genomic DNA of the biological sample with a quantitative amplification technique using a primer pair comprising a first oligonucleotide primer and a second oligonucleotide primer, wherein at least one oligonucleotide primer of the primer pair specifically hybridizes to the transgene; and (c) detecting and/or quantifying the genomic nucleic acid that was amplified through step (b).

43. The method according to claim 15, wherein the method further comprises evaluating the validity of an assay for quantifying the integration of a recombinant vector nucleic acid by assessing one or more assay acceptance criteria selected from the group consisting of:

(a) the threshold cycle of both the recombinant vector nucleic acid and the reference polynucleotide sequence in all the replicates of a control containing no template DNA is undeterminable;

(b) the correlation coefficient for the standard curves of both the recombinant vector nucleic acid and the reference polynucleotide sequence, generated by linear regression using the standard samples, is greater than or equal to 0.97;

(c) the estimated copy values for the recombinant vector nucleic acid and the reference polynucleotide sequence from the slope of said standard curves indicates a PCR efficiency of between 90% and 110%;

(d) the threshold cycle of both the recombinant vector nucleic acid and the reference polynucleotide sequence in none of the replicates of any of the standard samples is undeterminable;

(e) the mean threshold cycle of both the recombinant vector nucleic acid and the reference polynucleotide sequence in the base standard sample is less than or equal to 22.0;

(f) the standard deviation in the threshold cycle of both the recombinant vector nucleic acid and the reference polynucleotide sequence in each standard sample is less than or equal to 0.60;

(g) the average measured copies of the reference polynucleotide sequence for the one or more positive control samples is within 30% of the nominal expected value;

(h) the measured mean VCN/cell value for the one or more positive control samples is within 30% of the nominal expected VCN/cell value for each control; and (i) the coefficient of variation of the VCN/cell value for the one or more positive control samples is less than or equal to 20%.

44. The method according to claim 15, wherein the method further comprises evaluating the validity of the quantification of the integration of a recombinant vector nucleic acid for a sample by assessing one or more sample acceptance criteria selected from the group consisting of:

(a) the average copy value of the reference polynucleotide sequence in the sample is within 30% of the expected value of 30,303.030 copies;

(b) if the sample has a genomic DNA (gDNA) concentration less than 0.02 µg/uL, the expected copies of the reference polynucleotide sequence for that sample is calculated from the amount of DNA actually loaded into the reactions;

(c) the mean target recombinant vector nucleic acid copy value in the sample is between the validated range of the copy value for the assay;

(d) the mean target recombinant vector nucleic acid copy value in the sample is between 121,212.121 and 193.939 copies;

(e) the coefficient of variation of the VCN/cell value for the replicates of the target sample is less than or equal to 20%; and (f) the standard deviation in the cycle threshold of both the target recombinant vector nucleic acid and the target reference polynucleotide sequence in the sample is less than or equal to 0.60.

45. The method according to claim 35, wherein the chimeric antigen receptor is a polypeptide encoded by a nucleic acid sequence comprising the sequence of SEQ ID NO: 19 or 21.

46. The method according to claim 42, wherein the transgene is a polypeptide encoded by a nucleic acid sequence comprising the sequence of SEQ ID NO: 19 or 21.

\* \* \* \* \*

```
                          SEQUENCE LISTING

<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctaattcact cccaacgaag acaag                                          25

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
ggtttccctt tcgctttcaa g                                                    21

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cgccactgct agagat                                                          16

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gcttgtactg ggtctctctg gttagac                                              27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgctttttg cttgtactgg g                                                    21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagagagctc ctctggtttc c                                                    21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ctttcaagtc cctgttcggg cgcc                                                 24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcatctcttg tgggctgtaa tc                                                   22

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgctggttct ctttcactga c                                                     21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
agggagagat ttgtgtgggc atgac                                                 25

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gatttgtgtg ggcatgac                                                         18

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ccctgttcgg gcgcc                                                            15

<210> SEQ ID NO 13
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ctggaagggc taattcactc ccaacgaaga caagatctgc tttttgcttg tactgggtct     60
ctctggttag accagatctg agcctgggag ctctctggct aactagggaa cccactgctt    120
aagcctcaat aaagcttgcc ttgagtgctt caagtagtgt gtgcccgtct gttgtgtgac    180
tctggtaact agagatccct cagacccttt tagtcagtgt ggaaaatctc tagcagtggc    240
gcccgaacag ggacttgaaa gcgaaaggga aaccagagga gctctctcga cgcaggactc    300

<210> SEQ ID NO 14
<211> LENGTH: 19
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 14
tgcttgtact gggtctctc                                                    19

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcgccactgc tagagatt                                                     18

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tgccttgagt gcttcaagta gtgtgt                                            26

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tgcttcaagt agtgtgt                                                      17

<210> SEQ ID NO 18
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110
```

```
Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Glu Val Gln Leu Val Glu Ser Gly Gly Gly Leu Val Gln Ala Gly
145                 150                 155                 160

Gly Ser Leu Arg Leu Ser Cys Ala Ala Ser Gly Arg Thr Phe Thr Met
                165                 170                 175

Gly Trp Phe Arg Gln Ala Pro Gly Lys Glu Arg Glu Phe Val Ala Ala
            180                 185                 190

Ile Ser Leu Ser Pro Thr Leu Ala Tyr Tyr Ala Glu Ser Val Lys Gly
            195                 200                 205

Arg Phe Thr Ile Ser Arg Asp Asn Ala Lys Asn Thr Val Val Leu Gln
    210                 215                 220

Met Asn Ser Leu Lys Pro Glu Asp Thr Ala Leu Tyr Tyr Cys Ala Ala
225                 230                 235                 240

Asp Arg Lys Ser Val Met Ser Ile Arg Pro Asp Tyr Trp Gly Gln Gly
            245                 250                 255

Thr Gln Val Thr Val Ser Ser Thr Ser Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 19
<211> LENGTH: 1467
<212> TYPE: DNA
<213> ORGANISM: Artificial Sequence
<220> FEATURE:
<223> OTHER INFORMATION: Description of Artificial Sequence: Synthetic -continued

```
        polynucleotide

<400> SEQUENCE: 19
atggctctgc ccgtcaccgc tctgctgctg cctctggctc tgctgctgca cgctgctcgc        60
cctcaggtca aactggaaga atctggcgga ggcctggtgc aggcaggacg gagcctgcgc       120
ctgagctgcg cagcatccga gcacaccttc agctcccacg tgatgggctg gtttcggcag       180
gccccaggca aggagagaga gagcgtggcc gtgatcggct ggagggacat ctccacatct       240
tacgccgatt ccgtgaaggg ccggttcacc atcagccggg acaacgccaa gaagacactg       300
tatctgcaga tgaacagcct gaagcccgag gacaccgccg tgtactattg cgcagcaagg       360
agaatcgacg cagcagactt tgattcctgg ggccagggca cccaggtgac agtgtctagc       420
ggaggaggag gatctgaggt gcagctggtg gagagcggag cggcctggt gcaggccgga       480 ggctctctga ggctgagctg tgcagcatcc ggaagaacct tcacaatggg ctggtttagg       540
caggcaccag aaaggagag ggagttcgtg gcagcaatca gcctgtcccc taccctggcc       600
tactatgccg agagcgtgaa gggcaggttt accatctccc gcgataacgc caagaataca       660
gtggtgctgc agatgaactc cctgaaacct gaggacacag ccctgtacta ttgtgccgcc       720
gatcggaaga gcgtgatgag cattagacca gactattggg ggcagggaac acaggtgacc       780
gtgagcagca ctagtaccac gacgccagcg ccgcgaccac caacaccggc gcccaccatc       840
gcgtcgcagc ccctgtccct gcgcccagag gcgtgccggc cagcggcggg gggcgcagtg       900
cacacgaggg ggctggactt cgcctgtgat atctacatct gggcgccctt ggccgggact       960 tgtgggggtcc ttctcctgtc actggttatc acccttact gcaaacgggg cagaaagaaa      1020
ctcctgtata tattcaaaca accatttatg agaccagtac aaactactca gaggaagat       1080 ggctgtagct gccgatttcc agaagaagaa gaaggaggat gtgaactgag agtgaagttc      1140
agcaggagcg cagacgcccc cgcgtaccag cagggccaga accagctcta taacgagctc      1200
aatctaggac gaagagagga gtacgatgtt ttggacaaga cgtggccg ggaccctgag      1260 atggggggaa agccgagaag gaagaaccct caggaaggcc tgtacaatga actgcagaaa      1320
gataagatgg cggaggccta cagtgagatt gggatgaaag cgagcgccg gagggggcaag      1380 gggcacgatg gcctttacca gggtctcagt acagccacca aggacaccta cgacgccctt      1440
cacatgcagg ccctgccccc tcgctaa                                          1467
```

```
<210> SEQ ID NO 20
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Phe Gly Val Pro
    50                  55                  60

Asp Arg Phe Ser Gly Ser Gly Ala Gly Thr Asp Phe Thr Leu Lys Ile
65                  70                  75                  80
```

```
Ser Arg Val Glu Ala Glu Asp Val Gly Val Tyr Tyr Cys Met Gln Ala
            85                  90                  95

Thr Gln Phe Pro His Thr Phe Gly Gln Gly Thr Lys Leu Glu Ile Lys
            100                 105                 110

Gly Gly Ser Glu Gly Lys Ser Ser Gly Ser Gly Ser Glu Ser Lys Ser
            115                 120                 125

Thr Gly Gly Ser Gln Val Thr Leu Lys Glu Ser Gly Pro Val Leu Val
    130                 135                 140

Lys Pro Thr Glu Thr Leu Thr Leu Thr Cys Thr Val Ser Gly Phe Ser
145                 150                 155                 160

Leu Thr Asn Ile Arg Met Ser Val Ser Trp Ile Arg Gln Pro Pro Gly
                165                 170                 175

Lys Ala Leu Glu Trp Leu Ala His Ile Phe Ser Asn Asp Glu Lys Ser
            180                 185                 190

Tyr Ser Ser Ser Leu Lys Ser Arg Leu Thr Ile Ser Arg Asp Thr Ser
            195                 200                 205

Lys Ser Gln Val Val Leu Thr Leu Thr Asn Val Asp Pro Val Asp Thr
    210                 215                 220

Ala Thr Tyr Tyr Cys Ala Arg Met Arg Leu Pro Tyr Gly Met Asp Val
225                 230                 235                 240

Trp Gly Gln Gly Thr Thr Val Thr Val Ser Ser Thr Ser Thr Pro Ala
            245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
    290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
            355                 360                 365

Ser Ala Asp Ala Pro Ala Tyr Lys Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470
```

<210> SEQ ID NO 21
<211> LENGTH: 1482

-continued

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atggcttggg tgtggacctt gctattcctg atggcagctg cccaaagtat acaggccgac        60
attgtgatga cccaaacacc tcttagtagt cctgtaactc tcggacagcc agcttcaata       120
tcttgtcgct caagtcaatc cctcgtccat tccgacggca cacctacct ctcttggctc        180 caacagagac ccggccagcc tcccagactt ctcatctaca aaatcagtaa caggttcttc       240
ggcgtccctg acaggttcag tggatctgga gcaggtacag atttcacctt gaagataagt       300
agagtggagg ctgaggacgt aggcgtctat tattgtatgc aagctaccca attcccacat       360
acattcggcc aaggcactaa attggaaata aaaggcggct ccgagggcaa gagcagcggc       420
agcggcagcg agagcaagag caccggcggc agccaagtaa cactcaagga gagcggacca       480
gtcttggtga aaccaactga gaccttgact ttgacatgta ctgtaagtgg cttcagcctt       540
accaacatca ggatgtcagt atcttggata aggcaaccac ctggcaaggc actcgaatgg       600
ctggcacaca tcttttctaa cgacgaaaaa tcctattctt ccagtctcaa aagtcgcctt       660
accatcagcc gagataccag taagagtcaa gtagttctta cattgaccaa tgtagatcca       720
gttgatacag ccacatacta ctgcgcacga atgcggcttc catacggcat ggatgtatgg       780
ggacagggaa ctactgttac cgttagttcc actagtaccc cagccccacg ccctcccacc       840
cctgctccta caatagcatc ccagcccttg tcacttcgcc ccgaagcatg cagaccagcc       900
gcaggcggtg ctgtgcatac ccgaggactg gacttcgcct gcgacatcta catctgggcc       960
ccactggccg gcacctgcgg cgtgctgctg ctgagcctgg tgatcaccct gtactgcaag      1020
cgcggccgca agaagctgct gtacatcttc aagcagccat tcatgcgccc agtgcagacc      1080
acccaggagg aggacggctg cagctgccgc ttcccagagg aggaggaggg cggctgcgag      1140
ctgcgcgtga gttcagccg cagcgccgac gccccagcct acaagcaggg ccagaaccag      1200
ctgtacaacg agctgaacct gggccgccgc gaggagtacg acgtgctgga caagcgccgc      1260
ggccgcgacc cagagatggg cggcaagcca cgccgcaaga acccacagga gggcctgtac      1320
aacgagctgc agaaggacaa gatggccgag gcctacagcg agatcggcat gaagggcgag      1380
cgccgccgcg caagggcca cgacggcctg taccagggcc tgagcaccgc caccaaggac      1440
acctacgacg ccctgcacat gcaggccctg ccaccacgct ga                        1482
```

<210> SEQ ID NO 22
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
```

-continued

```
          50                55                60

Ser Gly Ser Gly Thr Glu Phe Thr Leu Thr Ile Ser Ser Leu Gln Pro
65                70                75                80

Glu Asp Phe Ala Thr Tyr Tyr Cys Gln Gln Leu Asn Ser Tyr Pro Arg
                85                90                95

Thr Phe Gly Gln Gly Thr Lys Val Glu Ile Lys Gly Gly Ser Glu Gly
            100               105               110

Lys Ser Ser Gly Ser Gly Ser Glu Ser Lys Ser Thr Gly Gly Ser Glu
        115               120               125

Val Gln Leu Val Glu Ser Gly Gly Gly Leu Val Gln Pro Gly Gly Ser
    130               135               140

Leu Arg Leu Ser Cys Ala Ala Ser Gly Phe Thr Phe Ser Ser Tyr Trp
145               150               155               160

Met Thr Trp Val Arg Gln Ala Pro Gly Lys Gly Leu Glu Trp Val Ala
                165               170               175

Asn Ile Lys Gln Asp Gly Ser Glu Arg Tyr Tyr Val Asp Ser Val Lys
                180               185               190

Gly Arg Phe Thr Ile Ser Arg Asp Asn Ala Lys Asn Ser Leu Tyr Leu
                195               200               205

Gln Met Asn Ser Leu Arg Ala Glu Asp Thr Ala Val Tyr Tyr Cys Ala
    210               215               220

Arg Asp Gln Asn Tyr Asp Ile Leu Thr Gly His Tyr Gly Met Asp Val
225               230               235               240

Trp Gly Gln Gly Thr Thr Val Thr Val Ser Ser Thr Ser Thr Pro Ala
                245               250               255

Pro Arg Pro Pro Thr Pro Ala Pro Thr Ile Ala Ser Gln Pro Leu Ser
                260               265               270

Leu Arg Pro Glu Ala Cys Arg Pro Ala Ala Gly Gly Ala Val His Thr
                275               280               285

Arg Gly Leu Asp Phe Ala Cys Asp Ile Tyr Ile Trp Ala Pro Leu Ala
    290               295               300

Gly Thr Cys Gly Val Leu Leu Leu Ser Leu Val Ile Thr Leu Tyr Cys
305               310               315               320

Lys Arg Gly Arg Lys Lys Leu Leu Tyr Ile Phe Lys Gln Pro Phe Met
                325               330               335

Arg Pro Val Gln Thr Thr Gln Glu Glu Asp Gly Cys Ser Cys Arg Phe
                340               345               350

Pro Glu Glu Glu Glu Gly Gly Cys Glu Leu Arg Val Lys Phe Ser Arg
            355               360               365

Ser Ala Asp Ala Pro Ala Tyr Lys Gln Gly Gln Asn Gln Leu Tyr Asn
    370               375               380

Glu Leu Asn Leu Gly Arg Arg Glu Glu Tyr Asp Val Leu Asp Lys Arg
385               390               395               400

Arg Gly Arg Asp Pro Glu Met Gly Gly Lys Pro Arg Arg Lys Asn Pro
                405               410               415

Gln Glu Gly Leu Tyr Asn Glu Leu Gln Lys Asp Lys Met Ala Glu Ala
            420               425               430

Tyr Ser Glu Ile Gly Met Lys Gly Glu Arg Arg Arg Gly Lys Gly His
        435               440               445
```

-continued

```
Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470
```